United States Patent
Vignon et al.

(10) Patent No.: US 11,950,960 B2
(45) Date of Patent: Apr. 9, 2024

(54) ULTRASOUND IMAGING WITH DEEP LEARNING-BASED BEAMFORMING AND ASSOCIATED DEVICES, SYSTEMS, AND METHODS

(71) Applicant: KONINKLIJKE PHILIPS N.V., Eindhoven (NL)

(72) Inventors: Francois Guy Gerard Marie Vignon, Andover, MA (US); Muhammad Usman Ghani, Boston, MA (US); Jun Seob Shin, Winchester, MA (US); Faik Can Meral, Mansfield, MA (US); Sheng-Wen Huang, Ossining, NY (US); Jean-Luc Francois-Marie Robert, Cambridge, MA (US)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 410 days.

(21) Appl. No.: 17/423,872

(22) PCT Filed: Feb. 10, 2020

(86) PCT No.: PCT/EP2020/053288
§ 371 (c)(1),
(2) Date: Jul. 18, 2021

(87) PCT Pub. No.: WO2020/169384
PCT Pub. Date: Aug. 27, 2020

(65) Prior Publication Data
US 2022/0096054 A1 Mar. 31, 2022

Related U.S. Application Data

(60) Provisional application No. 62/809,080, filed on Feb. 22, 2019.

(51) Int. Cl.
*A61B 8/08* (2006.01)
*G06N 3/045* (2023.01)
*G06T 7/00* (2017.01)

(52) U.S. Cl.
CPC .......... *A61B 8/5207* (2013.01); *G06N 3/045* (2023.01); *G06T 7/0012* (2013.01);
(Continued)

(58) Field of Classification Search
CPC .... A61B 8/5207; G06N 3/045; G06T 7/0012; G06T 2207/10136; G06T 2207/20081;
(Continued)

(56) References Cited

U.S. PATENT DOCUMENTS 5,997,479 A * 12/1999 Savord ................. A61B 8/4488
600/447
8,348,846 B2 * 1/2013 Gunther ............... A61B 8/4245
600/443

(Continued)

OTHER PUBLICATIONS

International Search report and Written Opinion of PCT/E2020/053288, dated Jun. 25, 2020.
(Continued)

*Primary Examiner* — Sanjay Cattungal

(57) ABSTRACT

Ultrasound image devices, systems, and methods are provided. An ultrasound imaging system, comprising an array of acoustic elements configured to transmit ultrasound energy into an anatomy and to receive ultrasound echoes associated with the anatomy; and a processor circuit in communication with the array of acoustic elements and configured to receive, from the array, ultrasound channel data corresponding to the received ultrasound echoes; normalize the ultrasound channel data by applying a first scaling function to the ultrasound channel data; generate beamformed data by applying a predictive network to the normalized ultrasound channel data; de-normalize the beam-
(Continued)

formed data by applying a second scaling function to the beamformed data; generate an image of the anatomy from the beamformed data; and output, to a display in communication with the processor circuit, the image of the anatomy.

20 Claims, 13 Drawing Sheets

(52) U.S. Cl.
CPC ............... *G06T 2207/10136* (2013.01); *G06T 2207/20081* (2013.01); *G06T 2207/20084* (2013.01)

(58) Field of Classification Search
CPC ....... G06T 2207/20084; G01S 7/52028; G01S 7/52047; G01S 15/8915; G10K 11/346
See application file for complete search history.

(56) References Cited

U.S. PATENT DOCUMENTS

| | | | |
|---|---|---|---|
| 2002/0045820 A1* | 4/2002 | Pesque | G01S 7/5208 600/443 |
| 2009/0076379 A1* | 3/2009 | Hamill | A61B 6/032 600/463 |
| 2009/0216121 A1* | 8/2009 | Lacoste | A61B 8/4236 264/219 |
| 2009/0306502 A1* | 12/2009 | Lacoste | A61B 8/4236 600/439 |
| 2011/0009742 A1* | 1/2011 | Lachaine | A61N 5/1067 600/427 |
| 2011/0201934 A1* | 8/2011 | Robinson | G01S 7/5202 600/443 |
| 2014/0163374 A1* | 6/2014 | Ogasawara | A61B 8/0883 600/443 |
| 2020/0146656 A1* | 5/2020 | Gong | G01S 15/892 |
| 2020/0202518 A1* | 6/2020 | Vignon | G06T 5/50 |
| 2020/0234435 A1* | 7/2020 | Raynaud | A61B 8/483 |
| 2021/0077073 A1* | 3/2021 | El Kaffas | G06N 3/088 |
| 2022/0005258 A1* | 1/2022 | Mory | A61B 6/5223 |
| 2023/0172586 A1* | 6/2023 | Clingman | A61B 8/4494 600/407 |

OTHER PUBLICATIONS

Luchies, Adam C. et al "Deep neural networks for ultrasound beamforming." IEEE Transactions on Medical Imaging, vol. 37, No. 9, (2018), pp. 2010-2021.

Reiter, Austin et al, "A machine learning approach to identifying point source locations in photoacoustic data." Photons Plus Ultrasound: Imaging and Sensing 2017. vol. 10064.

Gasse, Maxime et al "High-quality plane wave compounding using convolutional neural networks." IEEE Transactions on Ultrasounds, Ferroelectrics and Frequency Control, vol. 64, No. 10 (2017): pp. 1637-1639.

Yoon, Yeo Hun, et al "Efficient B-mode Ultrasound Image Reconstruction from Sub-sampled RF Data using Deep Learning." IEEE Transactions on Medical Imaging (2018).

Kingma, Diederik et al."Adam: A Method for Stochastic Optimization", Conference Paper at ICLR 2015.

Luchies, Adam et al "Suppressing Off-Axis Scattering using Deep Neural Networks", Progress in Biomedicla Optical and Imaging, vol. 10580, Mar. 2018.

* cited by examiner

ULTRASOUND IMAGING WITH DEEP LEARNING-BASED BEAMFORMING AND ASSOCIATED DEVICES, SYSTEMS, AND METHODS

TECHNICAL FIELD

The present disclosure relates generally to ultrasound imaging and, in particular, to reconstructing ultrasound images from ultrasound echo channel responses using a predictive model for beamforming.

BACKGROUND

Ultrasound imaging systems are widely used for medical imaging. A conventional medical ultrasound system may include an ultrasound transducer probe coupled to a processing system and one or more display devices. The ultrasound transducer probe may include an array of acoustic elements that transmit acoustic waves into an object (e.g., a patient's body) and record acoustic waves reflected from the object. The transmission of the acoustic waves and/or the reception of reflected acoustic waves or echo responses can be performed by the same set of ultrasound transducer elements or different sets of acoustic elements. The processing system reconstructs or creates an image of the object from the echo responses received by the acoustic elements. For conventional ultrasound imaging, the processing system may perform beamforming by delaying and summing the received echo response signals to achieve receive focusing along imaging depths. The processing system may reconstruct the image from the beamformed signals by applying signal processing and/or image processing techniques.

There are often tradeoffs between resolution, contrast, penetration depth, signal-to-noise ratio (SNR), and/or acquisition speed or frame rate in conventional ultrasound imaging. For example, image quality or resolution in conventional ultrasound imaging is limited by diffraction. One approach to reducing the effect of diffraction is to employ a transducer with a larger aperture size. In another example, an ultrasound imaging system may utilize unfocused ultrasound beams or diverging waves to illuminate a larger portion of a region of interest (ROI) with a single transmission in order to reduce image acquisition time. However, images obtained from a limited number of diverging waves can have a lower image quality than images obtained from focused imaging. Thus, the ultrasound image quality in a conventional ultrasound imaging system can be limited by the capability (e.g., the transducer aperture size) of the system and/or the acquisition process.

SUMMARY

While existing ultrasound imaging has proved useful for clinical guidance and diagnosis, there remains a need for improved systems and techniques for providing high-quality ultrasound images. Embodiments of the present disclosure provide a deep learning framework to map ultrasound echo channel signals to beamformed signals instead of performing conventional delay-and-sum (DAS)-based beamforming. For example, an imaging probe including a transducer array may be used for ultrasound imaging. The transducer array may include an array of acoustic elements that emit ultrasound pulses into an object (e.g., a patient's anatomy) and receive ultrasound channel signals corresponding to ultrasonic waves reflected from the object. A predictive network (e.g., a convolutional neural network (CNN)) can be trained to map the per-channel ultrasound echo channel signals to beamformed signals on a pixel-by-pixel basis. In an example, the per-channel ultrasound echo channel signals are time-aligned and normalized prior to applying the predictive network. Thus, the predictive network is trained to learn beamforming instead of amplitude mapping and/or time-delay mapping. For example, a transducer array of a certain aperture size and/or an acquisition with a certain number of transmit firings can provide a certain image quality using DAS-based beamforming. In an embodiment, the predictive network can be trained to provide beamformed signals with a higher image quality or resolution than the actual transducer aperture size in use can provide. In an embodiment, the predictive network is trained to provide beamformed signals with a higher image quality or resolution than the actual number of transmit firings used in an acquisition can provide. The predictive network can be trained using a combination of simulation data, data acquired from phantoms in experimental test setups, and/or data acquired from patients in clinical settings. The disclosed embodiments are suitable for use in two-dimensional (2D) imaging, three-dimensional (3D) volumetric imaging, focused imaging, and/or unfocused imaging.

In one embodiment, an ultrasound imaging system includes an array of acoustic elements configured to transmit ultrasound energy into an anatomy and to receive ultrasound echoes associated with the anatomy; and a processor circuit in communication with the array of acoustic elements and configured to receive, from the array, ultrasound channel data corresponding to the received ultrasound echoes; normalize the ultrasound channel data by applying a first scaling function to the ultrasound channel data based on signal levels of the ultrasound channel data; generate beamformed data by applying a predictive network to the normalized ultrasound channel data; de-normalize the beamformed data by applying a second scaling function to the beamformed data based on the signal levels of the ultrasound channel data; generate an image of the anatomy from the beamformed data; and output, to a display in communication with the processor circuit, the image of the anatomy.

In some embodiments, wherein the processor circuit is further configured to apply time delays to the normalized ultrasound channel data based on an imaging depth. In some embodiments, wherein the ultrasound channel data includes a plurality of samples for a plurality of channels, wherein the beamformed data includes a plurality of output values, wherein the processor circuit is further configured to select a subset of the plurality of samples based on an imaging depth, wherein the processor circuit normalizing the ultrasound channel data includes scaling a first signal level of a first sample of the subset of the plurality of samples based on second signal levels of the subset of the plurality of samples to produce a subset of the normalized ultrasound channel data, and wherein the processor circuit generating the beamformed data includes applying the predictive network to the subset of the normalized ultrasound channel data to produce a first output value of the plurality of output values in the beamformed data. In some embodiments, wherein the first sample and the first output value correspond to a same pixel location in the image. In some embodiments, wherein the processor circuit normalizing the ultrasound channel data includes scaling the first signal level of the first sample based on a root-mean-square (RMS) value of the subset of the plurality of samples. In some embodiments, wherein the array of acoustic elements includes a first aperture size, and wherein the beamformed data is associated with a second aperture size larger than the first aperture size. In some embodiments, wherein the predictive network is trained by providing test ultrasound channel data generated based on the first aperture size and first target beamformed data generated based on the second aperture size; and training the predictive network to produce the first target beamformed data from the test ultrasound channel data. In some embodiments, wherein the predictive network is trained by providing second target beamformed data generated based on the first aperture size; and training the predictive network to produce the second target beamformed data from the test ultrasound channel data before training the predictive network to produce the first target beamformed data. In some embodiments, wherein the ultrasound channel data is generated from a first quantity of ultrasound transmit trigger events, and wherein the beamformed data is associated with a second quantity of ultrasound transmit trigger events greater than the first quantity of ultrasound transmit trigger events. In some embodiments, wherein the predictive network is trained by providing test ultrasound channel data generated based on the first quantity of ultrasound transmit trigger events and first target beamformed data generated based on the second quantity of ultrasound transmit trigger events; and training the predictive network to produce the first target beamformed data from the test ultrasound channel data. In some embodiments, wherein the predictive network is trained by providing second target beamformed data generated based on the first quantity of ultrasound transmit trigger events; and training the predictive network to produce the second target beamformed data from the test ultrasound channel data before training the predictive network to produce the first target beamformed data. In some embodiments, wherein the ultrasound channel data is associated with a first signal-to-noise (SNR), and wherein the beamformed data is associated with a second SNR greater than the first SNR. In some embodiments, wherein the array of acoustic elements includes a one-dimensional array of acoustic elements. In some embodiments, wherein the array of acoustic elements includes a two-dimensional array of acoustic elements.

In one embodiment, a method of ultrasound imaging includes receiving, at a processor circuit in communication with an array of acoustic elements, ultrasound channel data corresponding to ultrasound echoes associated with an anatomy; normalizing the ultrasound channel data by applying a first scaling function to the ultrasound channel data based on signal levels of the ultrasound channel data; generating beamformed data by applying a predictive network to the normalized ultrasound channel data; de-normalizing the beamformed data by applying a second scaling function to the beamformed data based on the signal levels of the ultrasound channel data; generating an image of the anatomy from the beamformed data; and outputting, to a display in communication with the processor circuit, the image of the anatomy.

In some embodiments, the method further comprises applying time delays to the normalized ultrasound channel data based on an imaging depth. In some embodiments, wherein the ultrasound channel data includes a plurality of samples for a plurality of channels, wherein the beamformed data includes a plurality of output values, wherein the method includes selecting a subset of the plurality of samples based on an imaging depth, wherein the normalizing the ultrasound channel data includes scaling a first signal level of a first sample of the subset of the plurality of samples based on second signal levels of the subset of the plurality of samples to produce the normalized ultrasound channel data, the first sample corresponding to a pixel location in the image, and generating the beamformed data by applying the predictive network to the subset of the normalized ultrasound channel data to produce a first output value of the plurality of output values in the beamformed data, the first output value corresponding to the pixel location. In some embodiments, wherein the array of acoustic elements includes a first aperture size, and wherein the beamformed data is associated with a second aperture size larger than the first aperture size. In some embodiments, wherein the ultrasound channel data is generated from a first quantity of ultrasound transmit trigger events, and wherein the beamformed data is associated with a second quantity of ultrasound transmit trigger events greater than the first quantity of ultrasound transmit trigger events. In some embodiments, wherein the ultrasound channel data is associated with a first signal-to-noise (SNR), and wherein the beamformed data is associated with a second SNR greater than the first SNR.

Additional aspects, features, and advantages of the present disclosure will become apparent from the following detailed description.

BRIEF DESCRIPTION OF THE DRAWINGS

Illustrative embodiments of the present disclosure will be described with reference to the accompanying drawings, of which.

DETAILED DESCRIPTION

Figure 1:
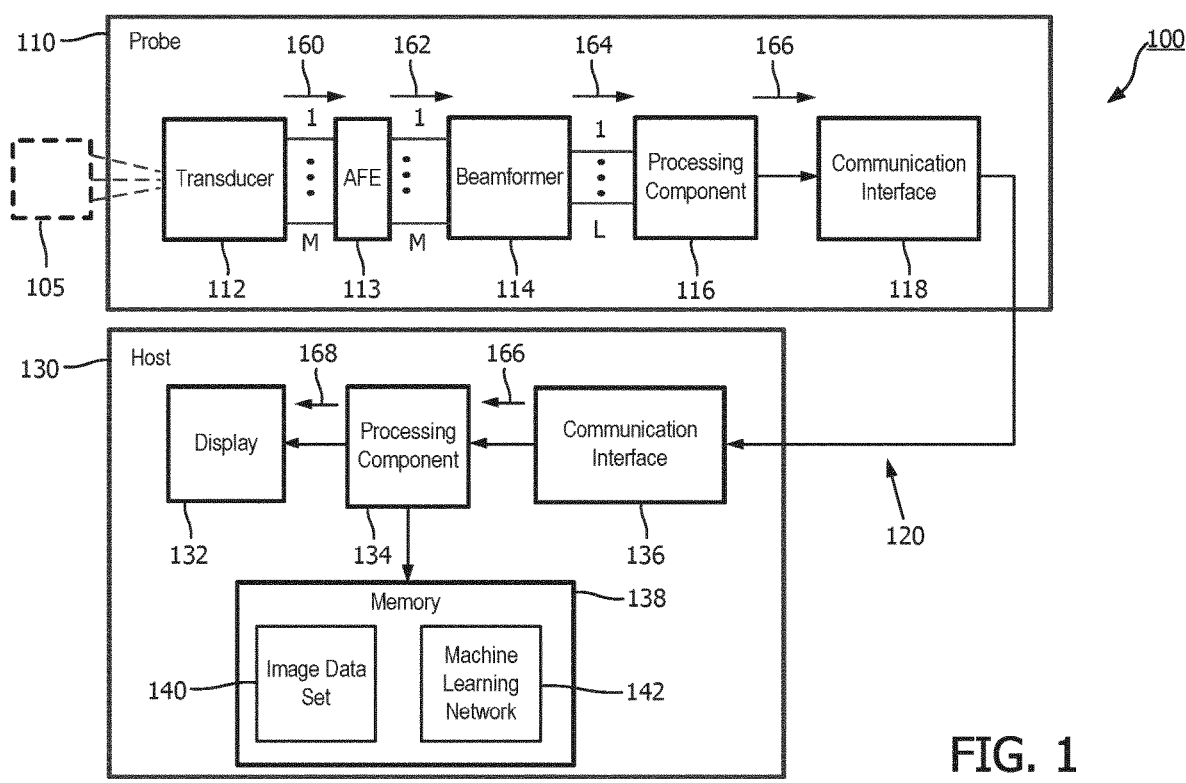
FIG. 1 is a schematic diagram of an ultrasound imaging system, according to aspects of the present disclosure.

For the purposes of promoting an understanding of the principles of the present disclosure, reference will now be made to the embodiments illustrated in the drawings, and specific language will be used to describe the same. It is nevertheless understood that no limitation to the scope of the disclosure is intended. Any alterations and further modifications to the described devices, systems, and methods, and any further application of the principles of the present disclosure are fully contemplated and included within the present disclosure as would normally occur to one skilled in the art to which the disclosure relates. In particular, it is fully contemplated that the features, components, and/or steps described with respect to one embodiment may be combined with the features, components, and/or steps described with respect to other embodiments of the present disclosure. For the sake of brevity, however, the numerous iterations of these combinations will not be described separately.

FIG. 1 is a schematic diagram of an ultrasound imaging system 100, according to aspects of the present disclosure. The system 100 is used for scanning an area or volume of a patient's body. The system 100 includes an ultrasound imaging probe 110 in communication with a host 130 over a communication interface or link 120. The probe 110 includes a transducer 112, an analog front end (AFE) 113, a beamformer 114, a processor circuit 116, and a communication interface 118. The host 130 includes a display 132, a processor circuit 134, a communication interface 136, and a memory 138.

The probe 110 may be in any suitable form for imaging various body parts of a patient while positioned inside or outside of the patient's body. In an embodiment, the probe 110 is an external ultrasound imaging device including a housing configured for handheld operation by a user. The transducer 112 can be configured to obtain ultrasound data while the user grasps the housing of the probe 110 such that the transducer 112 is positioned adjacent to and/or in contact with a patient's skin. The probe 110 is configured to obtain ultrasound data of anatomy within the patient's body while the probe 110 is positioned outside of the patient's body. In some other embodiments, the probe 110 may be in the form of a catheter, an intravascular ultrasound (IVUS) catheter, an intracardiac echocardiography (ICE) catheter, a transesophageal echocardiography (TEE) probe, a transthoracic echocardiography (TTE) probe, an endo-cavity probe, a handheld ultrasound scanner, or a patch-based ultrasound device.

The transducer 112 emits ultrasound signals towards an anatomical object 105 and receives echo signals reflected from the object 105 back to the transducer 112. The object 105 may include any anatomy (e.g., lung, blood vessel, tissues, heart, kidney, and/or liver) of a patient that is suitable for ultrasound imaging examination. The ultrasound transducer 112 can include any suitable number of acoustic elements, including one or more acoustic elements and/or plurality of acoustic elements. In some instances, the transducer 112 includes a single acoustic element. In some instances, the transducer 112 may include an array of acoustic elements with any number of acoustic elements in any suitable configuration. For example, the transducer 112 can include between 1 acoustic element and 1000 acoustic elements, including values such as 2 acoustic elements, 4 acoustic elements, 36 acoustic elements, 64 acoustic elements, 128 acoustic elements, 500 acoustic elements, 812 acoustic elements, and/or other values both larger and smaller. In some instances, the transducer 112 may include an array of acoustic elements with any number of acoustic elements in any suitable configuration, such as a linear array, a planar array, a curved array, a curvilinear array, a circumferential array, an annular array, a phased array, a matrix array, a one-dimensional (1D) array, a 1.x dimensional array (e.g., a 1.5D array), or a two-dimensional (2D) array. The array of acoustic elements (e.g., one or more rows, one or more columns, and/or one or more orientations) that can be uniformly or independently controlled and activated. The transducer 112 can be configured to obtain 1D, 2D, and/or three-dimensional (3D) images of patient anatomy. The acoustic elements may also be referred to as transducer elements or imaging elements. In some embodiments, the transducer 112 may include a piezoelectric micromachined ultrasound transducer (PMUT), capacitive micromachined ultrasonic transducer (CMUT), single crystal, lead zirconate titanate (PZT), PZT composite, other suitable transducer types, and/or combinations thereof.

The AFE 113 is coupled to the transducer 112. The AFE 113 may include components that control the transmissions of ultrasound waves at the transducer 112 and/or the receptions of echo responses at the transducer 112. For example, in a transmit path, the AFE 113 may include a digital-to-analog converter (DAC), filters, gain controls, and/or a high-voltage (HV) transmitter that drives or triggers ultrasound pulse emissions at the acoustic elements or transducer elements of the transducer 112. In a receive path, the AFE 113 may include gain controls, filters, amplifiers, and analog-to-digital converts (ADCs) that receive echo responses from the transducer elements of the transducer 112. The AFE 113 may further include a plurality of transmit/receive (T/R) switches that control the switching between transmit and receive at the transducer elements and prevent the high-voltage pulses from damaging the transducer elements for the transducer 112.

Figure 2:
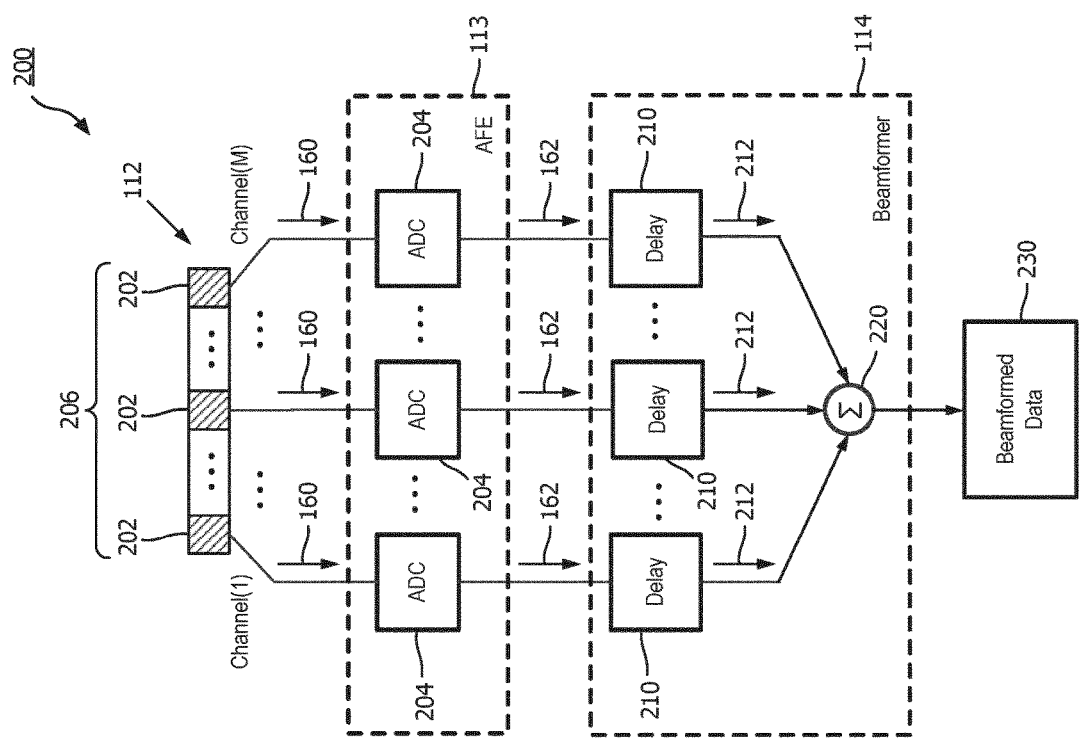
FIG. 2 is a schematic diagram of an ultrasound imaging system implementing delay-and-sum (DAS)-based beamforming, according to embodiments of the present disclosure.

In an embodiment, the transducer 112 includes M plurality of transducer elements (e.g., acoustic elements 202 of FIG. 2). In some embodiments, M can be about 2, 16, 64, 128, 192, or greater than 192. In the receive path, each transducer element can convert ultrasound energy received from a reflected ultrasound pulse to an electrical signal, forming a single receive channel. In other words, the transducer 112 can generate M analog ultrasound echo channel signals 160. The AFE 113 can be coupled to the transducer 112 via M signal lines. The ADCs (e.g., ADCs 204 of FIG. 2) in the AFE 113 can produce M digital ultrasound echo channel signals 162, each corresponding to an analog ultrasound echo channel signal 160 received at one of the transducer element in the transducer 112. The digital ultrasound echo channel signals 162 can also be referred to as ultrasound echo data streams or ultrasound echo channel data.

The beamformer 114 is coupled to the AFE 113. The beamformer 114 may include delay elements and summing elements configured to control transmit and/or receive beamforming at the transducer 112. The beamformer 114 may apply appropriate time-delays to at least a subset of the digital ultrasound echo channel signals 162 and combine the time-delayed digital ultrasound echo channel signals to form a beamformed signal 164 (e.g., a focused beam). For example, the beamformer 114 may produce L plurality of beamformed signals 164, where L is a positive integer smaller than M. In some embodiments, the beamformer 114 may include multiple stages of beamforming. For example, the beamformer 114 may perform partial beamforming to combine a subset of the digital ultrasound echo channel signals 162 to form partially beamformed signals and subsequently beamform the partial beamformed signals to produce fully beamformed signals. While the beamformer 114 is described in the context of digital beamforming, in some embodiments, the AFE 113 can include electronics and/or dedicated hardware for analog partial beamforming.

The processor circuit 116 is coupled to the beamformer 114. The processor circuit 116 may include a central processing unit (CPU), a digital signal processor (DSP), an application specific integrated circuit (ASIC), a controller, a field programmable gate array (FPGA) device, another hardware device, a firmware device, or any combination thereof configured to perform the operations described herein. The processor circuit 134 may also be implemented as a combination of computing devices, e.g., a combination of a DSP and a microprocessor, a plurality of microprocessors, one or more microprocessors in conjunction with a DSP core, or any other such configuration. The processor circuit 116 is configured to process the beamformed signals 164. For example, the processor circuit 116 may perform a series of coherent and/or in-coherent signal processing, such as compounding, envelope detection, logarithmic compression, and/or non-linear image filtering, to the beamformed signals 164 to produce image signals 166.

The communication interface 118 is coupled to the processor circuit 116. The communication interface 118 may include one or more transmitters, one or more receivers, one or more transceivers, and/or circuitry for transmitting and/or receiving communication signals. The communication interface 118 can include hardware components and/or software components implementing a particular communication protocol suitable for transporting signals over the communication link 120 to the host 130. The communication interface 118 can be referred to as a communication device or a communication interface module.

The communication link 120 may be any suitable communication link. For example, the communication link 120 may be a wired link, such as a universal serial bus (USB) link or an Ethernet link. Alternatively, the communication link 120 nay be a wireless link, such as an ultra-wideband (UWB) link, an Institute of Electrical and Electronics Engineers (IEEE) 802.11 WiFi link, or a Bluetooth link.

At the host 130, the communication interface 136 may receive the image signals 166, transducer element signals (e.g., the analog ultrasound echo channel signals 160), or partially beamformed signals. The communication interface 136 may be substantially similar to the communication interface 118. The host 130 may be any suitable computing and display device, such as a workstation, a personal computer (PC), a laptop, a tablet, or a mobile phone.

The processor circuit 134 is coupled to the communication interface 136. The processor circuit 134 may be implemented as a combination of software components and hardware components. The processor circuit 134 may include a central processing unit (CPU), a graphics processing unit (GPU), a digital signal processor (DSP), an application-specific integrated circuit (ASIC), a controller, a FPGA device, another hardware device, a firmware device, or any combination thereof configured to perform the operations described herein. The processor circuit 134 may also be implemented as a combination of computing devices, e.g., a combination of a DSP and a microprocessor, a plurality of microprocessors, one or more microprocessors in conjunction with a DSP core, or any other such configuration.

The processor circuit 134 can be configured to generate or reconstruct images 168 of the object 105 from the image signals 166 received from the probe 110, beamform images 168 from transducer signals (e.g., the analog ultrasound echo channel signals 160), or partially beamformed signals 164. The processor circuit 134 can further apply image processing techniques to the image signals 166. In some embodiments, the processor circuit 134 can perform scan conversions to form 2D or 2D volume images from the image signals 166. In some embodiments, the processor circuit 134 can perform real-time processing on the image signals 166 to provide a streaming video of ultrasound images 168 of the object 105. The images 168 can include morphological information, functional information, and/or quantitative measurement of the object 105 depending on the acquisition modalities used at the probe 110. The morphological information may include anatomical structural information (e.g., B-mode information) of the object 105. Examples of functional information may include tissue strain, elasticity, Doppler flow, tissue Doppler flow, and/or blood flow information associated with the object 105. Examples of quantitative measurements may include a blood flow velocity, blood flow volume, lumen diameter, lumen area, stenosis length, plaque burden, and/or tissue elasticity. In some embodiments, the processor circuit 134 can perform image analysis on the image signals 166 to determine clinical conditions associated with the object 105.

The display 132 is coupled to the processor circuit 134. The display 132 may be a monitor or any suitable display. The display 132 is configured to display ultrasound images, image videos, and/or information associated with the object 105 under examination.

While the system 100 is illustrated with beamforming and signal processing functions performed by the beamformer 114 and the processor circuit 116, respectively, at the probe 110, in some embodiments, at least some of the beamforming and/or signal processing functions may be performed at the host 130. In other words, the probe 110 may transfer digital ultrasound echo channel signals 162 or beamformed signals 164 to the host 130 for processing. In some other embodiments, the probe 110 may transfer the analog ultrasound echo channel signals 160, for example, with some gain controls, filtering, and/or partial analog beamforming to the host 130 for processing. In such embodiments, the host 130 may further include ADCs and a beamformer. In addition, the communication interface 118 at the probe 110 may be an industry standard physical connector and/or a proprietary physical connector and the communication link 120 may include any industry standard cables, coaxial cables, and/or proprietary cables. In general, the system 100 may represent any types of ultrasound imaging system, where ultrasound imaging functionalities may be partitioned in any suitable manner across a probe (e.g., including a transducer 112), a host, and/or any intermediate processing subsystem between the probe and the host.

According to embodiments of the present disclosure, the system 100 uses a predictive model (e.g., a deep learning model) for beamforming instead of the delay-and-sum (DAS)-based beamformer 114 described above. The system 100 can be used in various stages of ultrasound imaging. In an embodiment, the system 100 may be used for collecting ultrasound images to form a training dataset 140 for training a machine learning network 142 for ultrasound beamforming. For example, the host 130 may include a memory 138, which may be any suitable storage device, such as a cache memory (e.g., a cache memory of the processor circuit 134), random access memory (RAM), magnetoresistive RAM (MRAM), read-only memory (ROM), programmable read-only memory (PROM), erasable programmable read only memory (EPROM), electrically erasable programmable read only memory (EEPROM), flash memory, solid state memory device, hard disk drives, solid state drives, other forms of volatile and non-volatile memory, or a combination of different types of memory. The memory 138 can be configured to store the training image dataset 140 and the machine learning network 142. For example, the training image dataset 140 can store the digital ultrasound echo channel signals 162 in association with beamformed signals generated using the system 100 or simulated beamformed signals. In an embodiment, the system 100 may utilize the trained machine learning network 142 for beamforming instead of the DAS beamformer 114 in a clinical setting (e.g., during an ultrasound examination). Mechanisms for training a deep learning model for ultrasound beamforming and applying the trained deep learning model for ultrasound beamforming are described in greater detail herein.

FIG. 2 is a schematic diagram illustrating an ultrasound imaging system 200 implementing DAS-based beamforming, according to embodiments of the present disclosure. The system 200 corresponds to a portion of the system 100 and provides a more detailed view of components along the receive signal path of the system 100 (e.g., within the probe 110 and/or the host 130). As shown in FIG. 2, the transducer 112 includes a plurality of acoustic elements 202. Each acoustic element 202 forms a receive channel, where an analog ultrasound echo channel signal 160 may be received when the acoustic element 202 is activated for receiving after a transmit trigger. For example, the transducer 112 may include M quantity of acoustic elements 202. Thus, the receive channels can be referred to as Channel(1) to Channel (M). In an embodiment, the AFE 113 may include a plurality of ADCs 204. Each ADC 204 may be coupled to an acoustic element 202. While not shown, the AFE 113 may additionally include other components, such as filters and amplifiers, coupled to each acoustic element 202. Each ADC 204 may sample a corresponding analog ultrasound echo channel signal 160 to form a digital ultrasound echo channel signal 162. Each digital ultrasound echo channel signal 162 includes a series of samples along an imaging depth of field. In some other embodiments, the AFE 113 may include a less number of ADCs 204 than the number of receive channels. In such embodiments, each ADC 204 may be coupled to a subset of the receive channels and configured to sample analog ultrasound echo channel signals 160 from the subset of receive channels, for example, in a multiplexing manner.

The beamformer 114 is coupled to the ADCs 204. The beamformer 114 includes a plurality of delay elements 210 coupled to a summing element 220. Each delay element 210 is configured to apply a time-delay to a corresponding digital ultrasound echo channel signal 162 to produce a delayed ultrasound echo channel signal 212. The delay elements 210 may be dynamically configured to apply appropriate time-delays to the digital ultrasound echo channel signal 162. For example, one or more of the acoustic elements 202 may be triggered to transmit ultrasonic energy into an anatomy (e.g., the anatomy object 105) and a group of acoustic elements 202 may be activated to receive ultrasound echoes reflected from the anatomy due to the ultrasound signal transmission. Due to the different propagation paths, receive echoes may arrive at the acoustic elements 202 at different times. Thus, the delay elements 210 delays the ultrasound echo channel signal 162 such that the ultrasound echo channel signal 162 are aligned in time. The summing element 220 is configured to combine the delayed ultrasound echo channel signals 212 to produce beamformed data 230. The beamformed data 230 corresponds to the beamformed signals 164.

In general, the goal of beamforming is to reverse the acoustic wave propagation effect so that ultrasound or acoustic energy can be focused at various locations along a main axis of the ultrasound echo signal path. For example, the delay elements 210 can be dynamically configured to provide receive focusing at each echo location along the main axis of the ultrasound echo signal path. In other words, the delay elements 210 can be configured with different delays to provide focusing at different echo locations.

The beamformed data 230 can be further processed by the processor circuit 116 and/or the processor circuit 134, for example, including frequency compounding, envelope detection, logarithmic compression, and/or non-linear image filtering as described above with respect to FIG. 1, to produce an image 168.

Some performance measures, such as image quality or resolution and/or data acquisition rate or frame rates, may be important for ultrasound imaging. For example, the image quality, resolution, or contrast may impact a clinician's ability to differentiate anatomical details within an acquired ultrasound image. The data acquisition rate or frame rates may impact the amount of time required for acquiring an ultrasound image or video, and thus the real-time imaging capability and ultrasound examination time.

Ultrasound imaging quality or resolution can be limited by diffraction, which is determined by the aperture size of a transducer. In other words, the imaging quality or resolution of the systems 100 and/or 200 can be limited by the aperture size 206 (see FIG. 2) of the transducer 112 in use for an examination. The aperture size 206 refers to the physical size or dimensions of the transducer 112. The aperture size 206 may correspond to the number of acoustic elements 202 in the transducer 112. One approach to improving image quality or image resolution is to employ a transducer with a larger aperture size. In general, image resolution varies proportionally with transducer's aperture size. For example, a transducer having about 160 acoustic elements 202 can provide about twice the imaging resolution compared to a transducer having about 80 acoustic elements 202.

Data acquisition rates can be of a concern for 3D imaging or volumetric imaging, where a large amount of imaging data is acquired in order to produce a 3D image. Conventional ultrasound imaging acquisition schemes utilize focused transmit beams (shown in FIG. 3). A focused transmit beam can illuminate a limited region. Thus, multiple transmit beams are typically used to sweep through or illuminate an entire region of interest. As such, the use of focused transmit beams can pose a time limit for real-time volumetric imaging and/or applications where a high frame rate is important, for example, in cardiac imaging.

Figure 3:
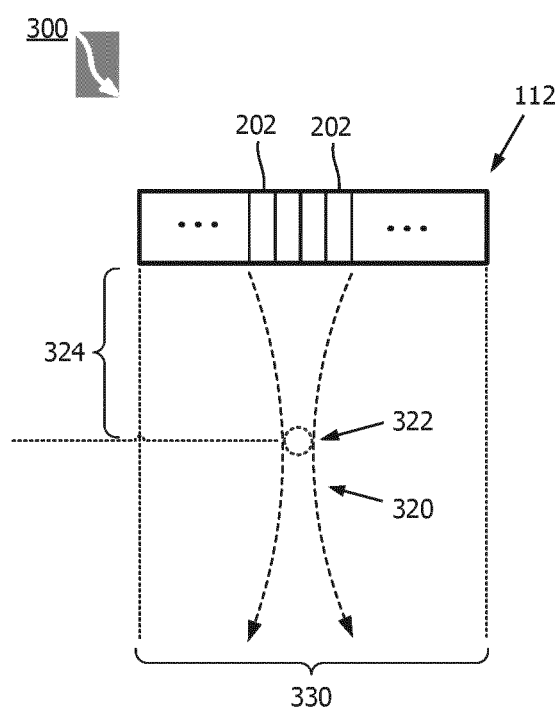
FIG. 3 is a schematic diagram illustrating an ultrasonic wave transmission scheme for ultrasound imaging, according to aspects of the present disclosure.

FIG. 3 is a schematic diagram illustrating an ultrasonic wave transmission scheme 300 for ultrasound imaging, according to aspects of the present disclosure. The scheme 300 can be employed by the systems 100 and/or 200. The scheme 300 configures the transducer 112 to emit a focused ultrasound beam 320 for ultrasound imaging. As shown, a group of acoustic elements 202 is activated to emit the focused ultrasound beam 320. The focused ultrasound beam 320 has an hour-glass shape with a focus 322 at an imaging depth of 324. As can be observed, multiple focused ultrasound beams 320 are required in order to sweep through a region of interest (ROI) 330, and thus may take a certain amount of time.

Figure 4:
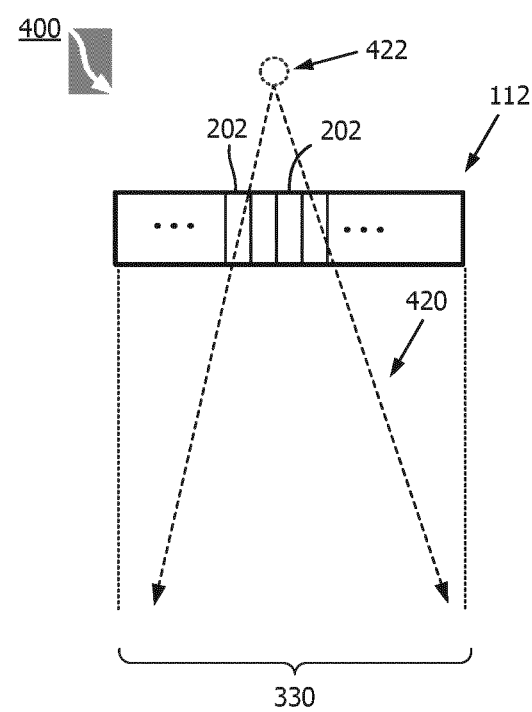
FIG. 4 is a schematic diagram illustrating an ultrasonic wave transmission scheme for ultrasound imaging, according to aspects of the present disclosure.

To improve the frame rates or reduce the image acquisition time, a faster imaging method may use unfocused ultrasound beams (shown in FIG. 4). An unfocused beam can illuminate a larger portion of the ROI 330, and thus may reduce the number of transmissions required to illuminate or sweep through the entire ROI 330.

FIG. 4 is a schematic diagram illustrating an ultrasonic wave transmission scheme 400 for ultrasound imaging, according to aspects of the present disclosure. The scheme 400 can be employed by the systems 100 and/or 200. The scheme 400 configures the transducer 112 to emit an unfocused ultrasound beam 420 for ultrasound imaging. As shown, a group of acoustic elements 202 is activated to produce the unfocused ultrasound beam 420. The unfocused ultrasound beam 420 includes plane waves or diverging waves, where the focus 422 is located behind the transducer 112. The unfocused ultrasound beam 420 can illuminate a large portion of the ROI 330 than the focused ultrasound beam 320, and thus a less number of transmissions is required to sweep the entire ROI 330 when using the unfocused ultrasound beam 420 compared to using the focused ultrasound beam 320.

While the diverging waves can illuminate a larger portion of the ROI 330, the image quality may degrade due to the lack of transmission focusing. One approach to compensating the image quality loss due to unfocused imaging is to repeat the transmission or increase the number of diverging wave transmissions and coherently compounding received beams from the multiple transmissions. Thus, there is a trade-off between frame rates or acquisition time and image quality.

The use of unfocused ultrasound beams 420 may have additional impacts with 3D imaging. 3D imaging uses a 2D transducer array, which may include a large number of acoustic elements (e.g., the acoustic elements 202), for example, in the order of thousands of acoustic elements. However, ultrasound imaging systems may typically have a limited number of system channels or receive channels (e.g., about 128) for transporting received ultrasound echoes received from the transducer to a processor circuit (e.g., the processor circuit 116 and/or the host 130). One approach to overcoming the limited number of system channels is to use micro-beamformers, where partial beamforming is performed prior to sending the received ultrasound echoes signals to the system channels. While micro-beamformers may provide a good receive focusing performance with the use of focused transmit beams (e.g., the beam 320), the receive focusing performance may be sub-optimal when the transmit beam is steered away from the main axis of the transmit beam (e.g., the unfocused beam 420). Further, in some instances, a micro-beamformed array may result in an under-sampled array, where the inter-element spacing (e.g., the spacing between the acoustic elements 202) may exceed the grating lobe limit of λ/2, where λ represents the wavelength of the transmit beam. As a result, grating lobes may appear in the reconstructed images. The grating lobes may not overlap with focused transmit beams, and thus may not be an issue when focused transmit beams are used. However, grating lobes can create artefacts with wider insonifications (e.g., when unfocused beams 420 are used).

Accordingly, the present disclosure provides techniques to overcome the image quality and data acquisition rate issues described above. The present disclosure uses deep learning techniques for beamforming instead of the conventional DAS-based beamforming. In one embodiment, a deep learning network is trained to map per-channel ultrasound echo data (e.g., the ultrasound echo channel signals 162) generated from a certain aperture size to beamformed data with a higher resolution than the aperture size can provide.

In other words, the deep learning-based beamformed data includes a resolution corresponding to images generated from a larger transducer aperture size (e.g., about twice the aperture size of the transducer used for collecting the per-channel ultrasound echo data). In one embodiment, a deep learning network is trained to map per-channel ultrasound echo data generated from unfocused transmit beams (e.g., the unfocused ultrasound beam 420) with a certain number of transmit triggering events to beamformed data with a higher image quality (e.g., a higher SNR, better contrast, and/or better contrast to noise) than number of transmit triggering events can provide. In other words, the deep learning-based beamformed data includes an image quality corresponding to images generated from a greater number of transmit triggering events. Accordingly, the present disclosure can improve image quality and/or reduce data acquisition time.

Figure 5:
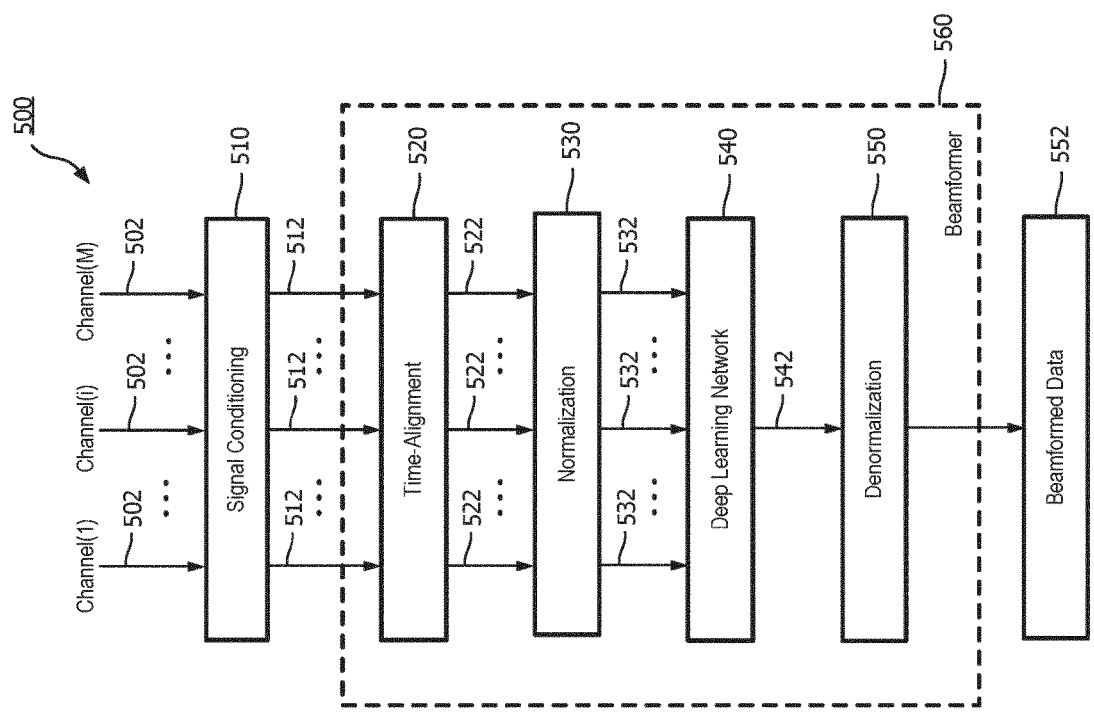
FIG. 5 is a schematic diagram of an ultrasound imaging system implementing deep learning-based beamforming, according to embodiments of the present disclosure.

FIG. 5 is a schematic diagram of an ultrasound imaging system 500 implementing deep learning-based beamforming, according to embodiments of the present disclosure. The system 500 is substantially similar to the system 100, but utilizes a deep learning-based beamformer 560 instead of the DAS-based beamformer 114 for beamforming. The system 500 includes a signal conditioning component 510 and the deep learning-based beamformer 560. The signal conditioning component 510 and the deep learning-based beamformer 560 can be implemented by a combination of hardware and software. The deep learning-based beamformer 560 includes a time-alignment component 520, a normalization component 530, a deep learning network 540, and a de-normalization component 550.

Similar to the systems 100 and 200, the system 500 may include a transducer array (e.g., the transducer 112). The transducer array may include M number of acoustic elements (e.g., the acoustic elements 202) that can be configured to transmit ultrasound energy into an anatomy (e.g., the anatomical object 105) and receive ultrasound echoes reflected from the anatomy back to the transducer array. The ultrasound echoes may be received in the form of M number of channels, each carrying an ultrasound echo channel signal 502 (e.g., the digital ultrasound echo channel signals 162). The ultrasound echo channel signals 502 may be raw radio frequency (RF) channel signals. The ultrasound echo channel signals 502 may be referred to as per-channel ultrasound RF echo data.

The signal conditioning component 510 can include one or more filters configured to receive the ultrasound echo channel signals 502 and condition the received ultrasound echo channel signals 502 prior to beamforming. In an example, the signal conditioning component 510 may apply a bandpass filter to the ultrasound echo channel signals 502 to remove electronic noise. The bandpass filter may span all quadrature band pass filters (QBPs) that are used by the system 500 for subsequent frequency compounding during image reconstruction. As an example, the transducer array may generate ultrasound beams at a center frequency of about 2.4 MHz and the ultrasound echo channel signals 502 are sampled at about 32 MHz (e.g., by ADCs such as the 204). The ultrasound echo channel signals 502 can be decimated at about 8 MHz to reduce subsequent computational speed requirements. Thus, the bandpass filter may be centered at about 2.4 MHz and may have a bandwidth between about 0 MHz and about 4 MHz. Typically, decimation can be performed after time-alignment since there are a greater number of samples available to make a more accurate estimation of delayed samples.

The time-alignment component 520 is coupled to the signal conditioning component 510. The time-alignment component 520 is configured to time-align the conditioned ultrasound echo channel signals 512. The time-alignment component 520 may include delay elements similar to the delay elements 210 and perform substantially similar time-delay operations as the delay elements 210 described above with respect to FIG. 2.

The normalization component 530 is coupled to the time-alignment component 520. The normalization component 530 is configured to normalize the signal levels of the time-aligned per-channel ultrasound echo signals 522 by scaling signal levels or amplitudes of the time-aligned per-channel ultrasound echo signals 522 by the local energy of the signals 522. The normalization component 530 performs the signal level normalization in subsets of samples from the time-aligned per-channel ultrasound echo signals 522, as described in greater detail herein.

The deep learning network 540 is coupled to the normalization component 530. The deep learning network 540 maps the normalized, time-aligned per-channel ultrasound echo signals 532 to normalized beamformed data 542. In an example, the deep learning network 540 can be a CNN network. Configurations or architectures of the deep learning network 540 and/or training of the deep learning network 540 are described in greater detail herein.

The applying of the deep learning network 540 to the normalized, time-aligned per-channel ultrasound echo channel signals 532 can reduce the complexity of the deep learning network 540 and improve the beamforming or beam-summing prediction performance of the deep learning network. For example, the performing of the time-alignment or time-delaying prior to the deep learning network 540 can allow the deep learning network 540 to be trained to learn beamforming without having to learn the time-alignment. The time-alignment or time-delay operations have relatively low computational complexity, and thus can be performed outside of the deep learning network 540 without a high computational cost. The normalization prior to the deep learning network 540 can avoid having samples with large amplitudes or signal levels dominate samples with lower amplitudes or signal levels. Thus, the deep learning network 540 can be trained to learn the summing operations in beamforming, and not amplitude mapping. As such, the normalization can prevent numerical imbalance in the loss function of the deep learning network 540. The loss function is a measure of how well the deep learning network 540 performs and is used as an error measure during training as described in greater detail herein.

The denormalization component 550 is coupled to the deep learning network 540. The denormalization component 550 is configured to de-normalize the beamformed data 542 based on the normalization performed at the normalization component 530. In other words, the de-normalization component 550 reverses the operations of the normalization component 530 as described in greater detail herein. The de-normalization component 550 produces de-normalized beamformed data 552. The beamformed data 552 can be further processed by the processor circuit 116 and/or the processor circuit 134, for examplaing, including frequency compounding, envelope detection, logarithmic compression, and/or non-linear image filtering as described above with respect to FIG. 1, to produce an image.

According to embodiments of the disclosure, the deep learning network 540 is trained such that the beamformed data 552 has a higher image quality or resolution than the DAS-based beamformed data 230. As such, images generated from the beamformed data 552 can have a higher image quality or resolution than images generated from the DAS-based beamformed data 230.

Figure 6:
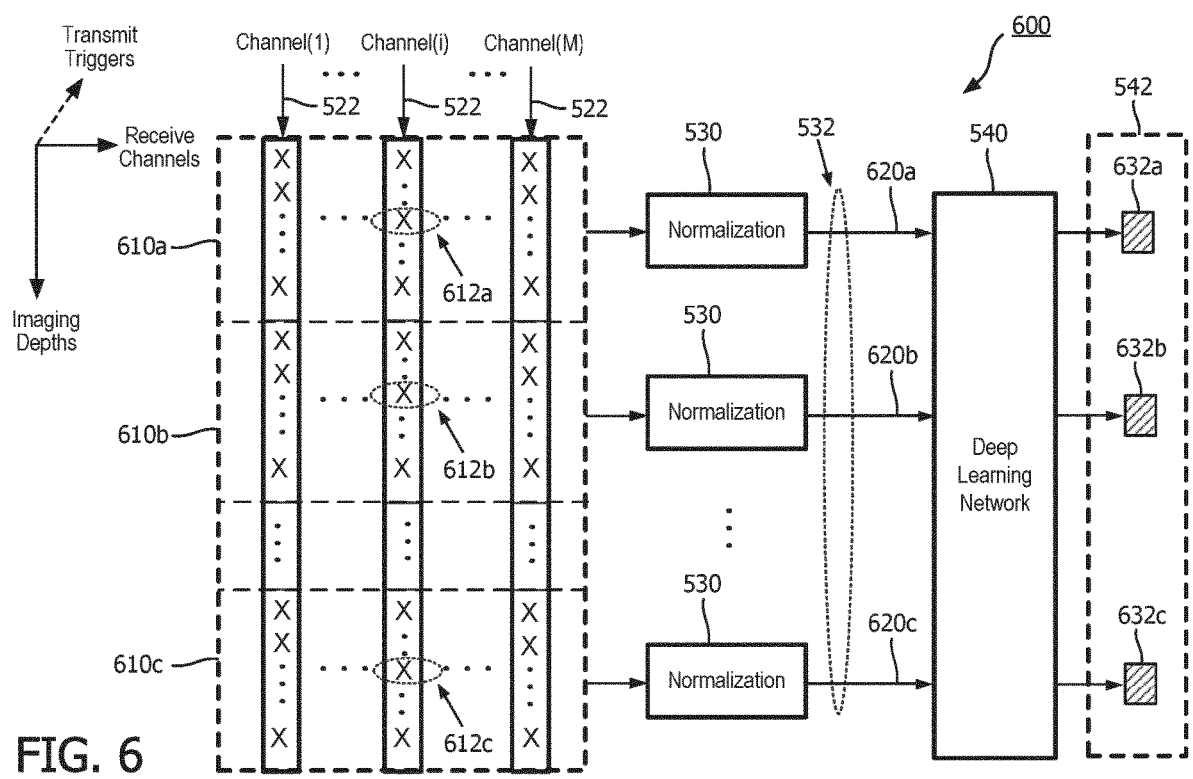
FIG. 6 is a schematic diagram illustrating a normalization scheme for deep learning-based beamforming, according to aspects of the present disclosure.

FIG. 6 is a schematic diagram illustrating a normalization scheme 600 for deep learning-based beamforming, according to aspects of the present disclosure. The scheme 600 is implemented by the normalization component 530 of FIG. 5. The scheme 600 applies normalization to the M channels of time-aligned ultrasound echo channel signals 522. Each ultrasound echo channel signal 522 in a receive channel includes a plurality of time samples along an imaging depth (e.g., in a y-dimension). The time samples are shown as symbols "X" in FIG. 6.

The scheme 600 partitions the samples in ultrasound echo channel signals 522 into multiple subsets 610 based on an imaging depth. For simplicity of discussion and illustration, three subsets 610a, 610b, and 610c are shown, each corresponding to an imaging depth range. However, the number of subsets 610 may vary depending on the embodiments. In some examples, the imaging depth range for each subset may correspond to about four times the wavelength (e.g., 4×λ) of a corresponding ultrasound transmission beam.

The normalization component 530 normalizes each subset 610 by scaling the signal levels or amplitudes of the samples in the corresponding subset 610 based on the signal energy of the corresponding subset 610. The normalization component 530 produces a subset of samples in the normalized ultrasound echo channel signals 532 from each subset 610. For example, the subset 610a is normalized to produce a subset 620a of the samples in the normalized ultrasound echo channel signals 532, the subset 610b is normalized to produce a subset 620b of samples in the normalized ultrasound echo channel signals 532, and the subset 610c is normalized to produce a subset 620c of samples in the normalized ultrasound echo channel signals 532. After the normalization, the normalized ultrasound echo channel signals 532 may include signal levels between about 1 and −1.

The deep learning network 540 is applied to the normalized ultrasound echo channel signals 532 to produce the beamformed data 542. As an example, the deep learning network 540 outputs a beamformed output sample or pixel 632a for the subset 610a, a beamformed output sample or pixel 632b for the subset 610b, and a beamformed output sample or pixel 632c for the subset 610c. The pixel 632a corresponds to a center time sample 612a of the subset 610a. The pixel 632b corresponds to a center time sample 612b of the subset 610b. The pixel 632c corresponds to a center time sample 612c of the subset 610c. In an example, the subset 610a includes about 13 samples for each channel along the imaging depths. The sample 612a may correspond to the $7^{th}$ sample in the Channel(i). The time sample 612a and the beamformed output pixel 632a may correspond to the same pixel location in the final image. Similarly, the time sample 612b and the beamformed output pixel 632b may correspond to the same pixel location in the final image. The time sample 612c and the beamformed output pixel 632c may correspond to the same pixel location in the final image.

In an embodiment, the normalization component 530 performs the scaling by dividing the subset of samples by the root-mean-square (RMS) of the signal level of a sample corresponding to a beamform output sample or pixel. For example, the normalization component 530 scales the sample 612a by dividing the sample 612a with the RMS of all the samples in subset 610a, scales the sample 612b by dividing the sample 612b with the RMS of all the samples in subset 610b, and scales the sample 612c by dividing the sample 612c with the RMS of all the samples in subset 610c.

Accordingly, each sample 612a, 612b, or 612c is sampled with respect to the signal energy in its neighborhood. Thus, the normalized echo channel signals 532 may mostly include samples with a signal energy between about 0 and about 1.

Referring to FIG. 5, for denormalization 550, the factor or RMS value used for the normalization of each subset 610 may be stored and the denormalization component 550 may apply the same factor or RMS value to each corresponding beamformed pixel value 632a, 632b, and 632c. In other words, the denormalization component 550 multiplies the output 632a by the RMS value of signal level of the subset 610a, multiplies the output 632b by the RMS value of signal level of the subset 610b, and multiplies the output 632c by the RMS value of signal level of the subset 610c.

While the subsets 610 are illustrated as non-overlapping in FIG. 6, the scheme 600 can be applied to overlapping samples in a sliding window manner along the imaging depths. As an example, the subset 610a may include K rows (e.g., row 1 to row K) of samples along the imaging depths. A second subset 610 may be formed by including samples from row 2 to row K+1 along the imaging depths. A third subset 610 may be formed by including samples from row 3 to row K+2 along the imaging depths and so forth. For each subset 610, a normalization value (e.g., RMS) is calculated from all the samples in the corresponding subset and the sample (e.g., the sample 612a) located in the center of the subset is divided by the normalization value. The denormalization may be performed using similar sliding window mechanisms. Thus, after applying the sliding windows to the normalization and the denormalization, all samples for the final beamformed data 552 are calculated.

In an embodiment, the deep learning network 540 is trained to map per-channel ultrasound echo data acquired from a transducer of a certain aperture size (e.g., the aperture size 206) or including a certain number of acoustic elements (e.g., the acoustic elements 202) to beamformed data corresponding to beamformed data obtained from a larger transducer aperture size (e.g., about double) or a greater number of acoustic elements. In other words, the beamformed data 552 predicted by the deep learning network 540 has a higher image quality (e.g., higher resolution and/or reduced clutters or artefacts) than what the transducer in use can provide.

While the scheme 600 is described in the context of a 2D dataset including a number of channels along the x-axis and imaging depths along the y-axis, similar mechanisms can be applied to a 3D dataset including a number of transmit triggers or firing along the z-axis, for example, when the deep learning network 540 is trained to map per-channel ultrasound echo data acquired from a certain number of transmit triggers to beamformed data corresponding to a greater number of transmit triggers. For example, the 3D dataset is partitioned into 3D data subsets based on imaging depths, the normalization component 530 may scale a center sample in each 3D data subset by dividing the centered sample with the RIVIS of all samples in the corresponding 3D subset, and the deep learning network 540 maps each 3D data subset to a beamformed output sample or pixel.

It should be noted that in some other embodiments, the normalization can be performed by scaling the entire set of ultrasound echo channel data (e.g., the ultrasound echo channel signals 522) based on a signal energy of the set of ultrasound echo channel data instead of applying the normalization per subset based on an imaging depth as in the scheme 600.

Figure 7:
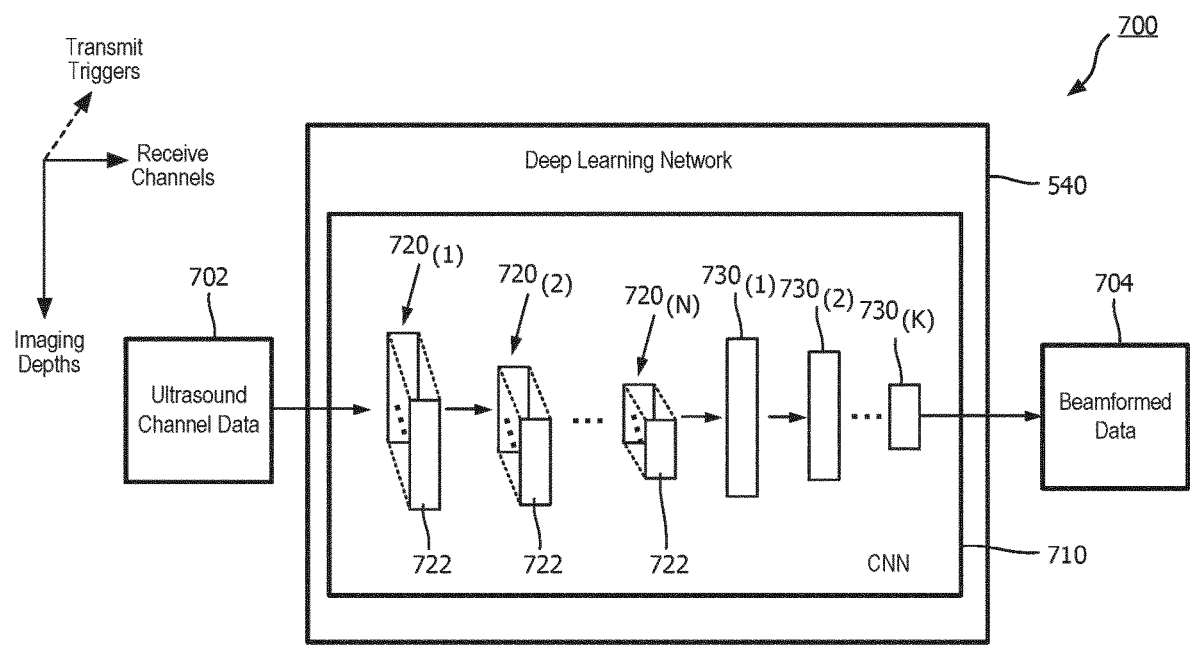
FIG. 7 is a schematic diagram illustrating a configuration of a deep learning network, according to aspects of the present disclosure.

FIG. 7 is a schematic diagram illustrating a configuration 700 of the deep learning network 540, according to aspects of the present disclosure. The deep learning network 540 may include one or more CNNs 710. The CNN 710 may operate on per-channel ultrasound channel data 702. The CNN 710 maps the per-channel ultrasound channel data 702 to beamformed data 704. In an example, the ultrasound channel data 702 may correspond to the normalized, time-aligned ultrasound echo channel signals 532 and the beamformed data 704 may correspond to the beamformed data 552 in the system 500. The CNN 710 provides per-channel pixel-based mapping of 2D data and/or 3D data to beamformed data.

The CNN 710 includes a set of N convolutional layers 720 followed by a set of K fully connected layers 730, where N and K may be any positive integers. The convolutional layers 720 are shown as $720_{(1)}$ to $720_{(N)}$. The fully connected layers 730 are shown as $730_{(1)}$ to $730_{(K)}$. In an example, the convolutional layers $720_{(1)}$ to $720_{(N)}$ and the fully connected layers 730 $730_{(1)}$ to $730_{(K-1)}$ may utilize a rectified non-linear (ReLU) activation function. The last output layer $730_{(K)}$ may utilize a linear activation function. Each convolutional layer 720 may include a set of filters 722 configured to extract features from the ultrasound channel data 702. The values N and K and the sizes of the filters 722 in each convolutional layer 720 may vary depending on the embodiments. It should be noted that the CNN 710 does not include pooling layers that are commonly used to reduce the size of the convolutional layers. The exclusion of pooling layers allows all convolutions to contribute to the output of the CNN 710. Alternatively the CNN may include convolutional layers 720 only, or fully connected layers 730 only.

In an example, the ultrasound channel data 702 may include a 2D dataset spanning an x-dimension corresponding to receive channels (e.g., Channel(1) to Channel (M) of FIGS. 2 and 5) and a y-dimension corresponding to imaging depths. The CNN 710 may include about five convolutional layers 720 (e.g., N=5) and about two fully connected layers 730 (e.g., K=2). The convolution layers 720 may include 2D convolutional kernels (e.g., the filters 722) spanning in the x and y dimensions. The 2D convolutional kernel size may vary depending on the embodiments. In some examples, the same 2D convolutional kernel size is used for all convolutional layers 720. In some examples, different 2D convolutional kernel sizes may be used for the convolutional layers 720. In some examples, the 2D convolutional kernel size may be dependent on the ultrasound transmission configuration used for collecting the ultrasound channel data 702. The first convolutional layer $720_{(1)}$ layer may include about sixty-four filters 722 or 2D convolutional kernels, the second convolutional layer $720_{(2)}$ layer may include about thirty-two filters 722, the third convolutional layer $720_{(3)}$ layer may include about sixteen filters 722, the fourth convolutional layer $720_{(4)}$ layer may include about eight filters 722, and the fifth convolutional layer $720_{(5)}$ layer may include about four filters 722. The first fully connected layer $730_{(1)}$ may have a size of about 32 and the last fully connected layer $730_{(2)}$ may have a size of about 1. The output at the last fully connected layer $730_{(2)}$ corresponds to a single beamformed output sample or pixel (e.g., the beamformed output 632a, 632b, or 632c).

In another example, the ultrasound channel data 702 may include a 3D dataset spanning an x-dimension corresponding to receive channels (e.g., Channel(1) to Channel (M) of FIGS. 2 and 5), a y-dimension corresponding to imaging depths, and a z-dimension corresponding to transmit triggers or transmit events. The CNN 710 may include about six convolutional layers 720 (e.g., N=6) and about four fully connected layers 730 (e.g., K=4). The convolution layers

720 may include 3D convolutional kernels spanning in the x, y, and z dimensions. The 3D convolutional kernel size may vary depending on the embodiments. In some examples, the same 3D convolutional kernel size is used for all convolutional layers 720. In some examples, different 3D convolutional kernel size may be used for the convolutional layers 720. In some examples, the 3D convolutional kernel size may be dependent on the ultrasound transmission configuration used for collecting the ultrasound channel data 702. The first convolutional layer $720_{(1)}$ layer may include about sixty-four filters 722 or 3D convolutional kernels, the second convolutional layer $720_{(2)}$ layer may include about thirty-two filters 722, the third convolutional layer $720_{(3)}$ layer may include about sixteen filters 722, the fourth convolutional layer $720_{(4)}$ layer may include about eight filters 722, the fifth convolutional layer $720_{(5)}$ layer may include about four filters 722, and the sixth convolutional layer $720_{(6)}$ layer may include about two filters 722. The first fully connected layer $730_{(1)}$ may have a size of about 32, the second fully connected layer $730_{(2)}$ may have a size of about 16, the third fully connected layer $730_{(3)}$ may have a size of about 8, and the last fully connected layer $730_{(4)}$ may have a size of about 1. The output at the last fully connected layer $730_{(4)}$ corresponds to a single beamformed output sample or pixel (e.g., the beamformed output 632a, 632b, or 632c).

In some examples, the CNN 710 may include a flattening layer at the output of the last convolutional layer $720_{(N)}$ to convert the convolutional part of the CNN 710 into a 1D feature vector for the subsequent fully connected layers 730. In some examples, the convolutional layers 720 can include zero padding such that the input and output size of the convolution or filter 722 are the same.

In some examples, the CNN 710 can include an additional layer before the first convolutional layer $720_{(1)}$ for normalization (e.g., including similar normalization operations as the normalization component 530) and an additional layer after the last fully connected layer $730_K$ for denormalization (e.g., including similar denormalization operations as the denormalization component 550). Thus, the CNN 710 can be applied without explicitly normalizing the time-align per-channel ultrasound echo signals (e.g., the signals 522) and without explicitly de-normalizing the output of the CNN 710. In some examples, the CNN 710 can be trained to perform beamforming including the pre-normalization layer and the post-denormalization layer for a particular ultrasound center frequency since the partitioning of ultrasound echo samples in the normalization can be dependent on the ultrasound center frequency.

Figure 8:
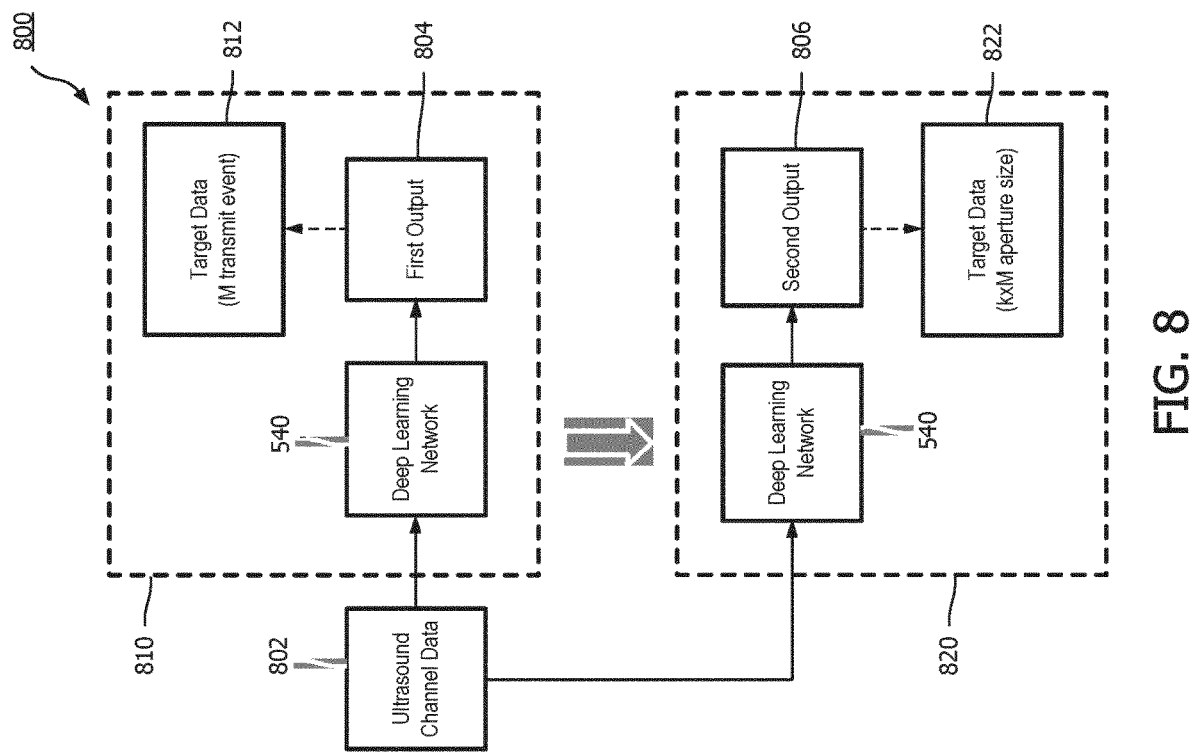
FIG. 8 is a schematic diagram illustrating a deep learning network training scheme, according to aspects of the present disclosure.

FIG. 8 is a schematic diagram illustrating a deep learning network training scheme 800, according to aspects of the present disclosure. The scheme 800 can be implemented by a computer system such as the host 130. The scheme 800 can be employed to train the deep learning network 540 for ultrasound beamforming. The scheme 800 trains the deep learning network 540 to predict or imitate beamformed data obtained from a transducer with a larger aperture size than a transducer in use.

The scheme 800 trains the deep learning network 540 in two stages 810 and 820. In the first stage 810, the scheme 800 trains the deep learning network 540 using an input-output pair, where the input includes ultrasound channel data 802 and the output includes target beamformed data 812. The ultrasound channel data 802 may be normalized, time-aligned ultrasound echo channel signals similar to the normalized, time-aligned ultrasound echo channel signals 532. The ultrasound channel data 802 may be acquired from a transducer array (e.g., the transducer 112) including an aperture size M (e.g., the aperture size 206) or M number of acoustic elements (e.g., the acoustic elements 202). The ultrasound channel data 802 may correspond to ultrasound echo responses received from a certain subject (e.g., the object 105). The ultrasound channel data 802 can be a 2D dataset with an x-dimension corresponding to receive channels and a y-dimension corresponding to imaging depths. The target data 812 may correspond to beamformed data generated from the ultrasound channel data 802 using a DAS-based beamformer (e.g., the beamformer 114). The target data 812 is also normalized so that the training does not have to learn amplitude mapping. During training, the deep learning network 540 can be applied to the ultrasound channel data 802 using forward propagation to produce an output 804 (e.g., the beamformed data 542). The coefficients of the filters 722 in the convolutional layers 720 and the weightings in the fully connected layers 730 can be adjusted using backward propagation to minimize the error between the predicted or mapped output 804 and the target output 812. In some embodiments, the error function or the loss function may be a mean-square-error (MSE) function or any other suitable error measure function. In other words, the scheme 800 trains the deep learning network 540 to approximate the beamforming provided by the beamformer 114. The training or the adjusting of the coefficients for the filters 722 may be repeated for multiple input-output pairs. The first stage 810 functions as an initialization of filter coefficients and/or weights in the deep learning network 540.

In the subsequent stage 820, the scheme 800 uses the filter coefficients and/or weights obtained for the deep learning network 540 from the first stage 810 as a start and continues with the training. The scheme 800 trains the deep learning network 540 using an input-output pair, where the input includes ultrasound channel data 802 and the output includes target beamformed data 822. The target data 822 may correspond to beamformed data of the same subject generated from a transducer with a larger aperture size than the aperture size M, for example, an aperture size of k×M or k×M number of acoustic elements, where k is greater than 1. Similarly, the target data 822 is normalized data. In an example, the target data 812 may be generated for an aperture size including about 80 acoustic elements (e.g., the acoustic elements 202) and the target data 822 may be generated for an aperture size including about 160 acoustic elements (e.g., based on the Tukey-apodization). Similar to the first stage 820, the deep learning network 540 is trained by applying the ultrasound channel data 802 using forward propagation to produce an output 806 (e.g., the beamformed data 542). The coefficients of the filters 722 in the convolutional layers 720 and the weightings in the fully connected layers 730 can be adjusted using backward propagation to minimize the error between the output 806 and the target output 822. The training or the adjusting of the coefficients for the filters 722 may be repeated for multiple input-output pairs. While the scheme 800 utilizes two stages of training, in some embodiments, the scheme 800 may perform the second stage 820 of training without performing the first stage 810 of the training.

As can be observed, the scheme 800 trains the deep learning network 540 to map per-channel ultrasound echo signals to beamformed data corresponding to a larger transducer aperture size than the aperture size of the transducer used for collecting the ultrasound echo channel signals. Accordingly, the deep learning network 540 can provide a higher image quality (e.g., improved resolution and/or enhanced contrast) in the final reconstructed images than a conventional DAS-based beamformer (e.g., the beamformed 114).

Figure 9:
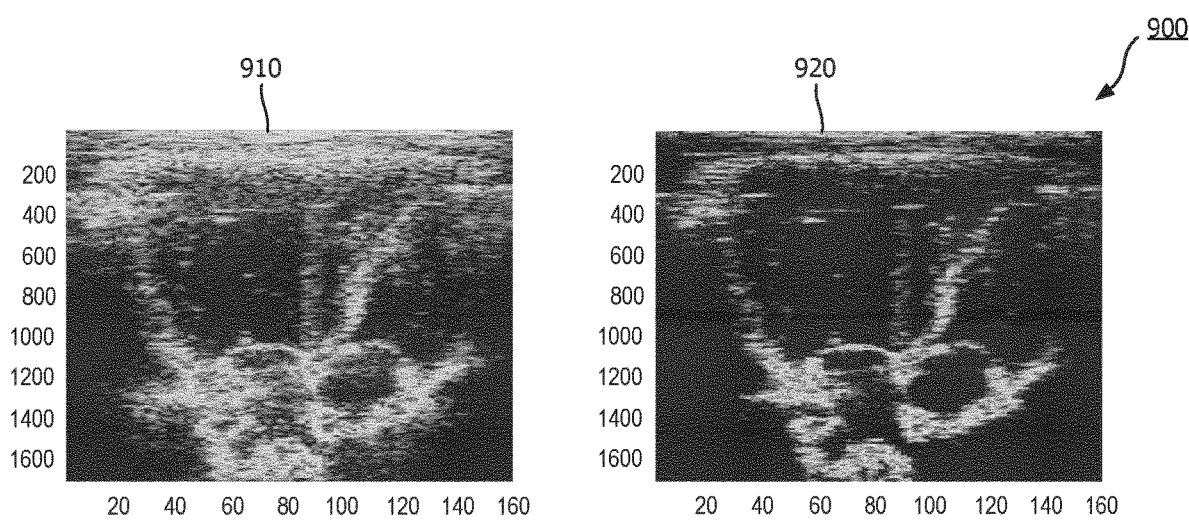
FIG. 9 illustrates pre-scan converted images generated from DAS-based beamforming and deep learning-based beamforming, according to aspects of the present disclosure.

FIG. 9 illustrates pre-scan converted ultrasound images generated from DAS-based beamforming and deep learning-based beamforming, according to aspects of the present disclosure. The ultrasound images 910 and 920 are generated from the same set of per-channel ultrasound echo signals (e.g., the digital ultrasound channel echo signals 162 and 502 and the ultrasound channel data 702 and 802) acquired from an in-vivo scan of a patient's heart in the apical four chamber view. The ultrasound image 910 is generated using a conventional DAS-based beamformer (e.g., the beamformer 114) to beamform the acquired per-channel ultrasound echo signals, whereas the ultrasound image 920 is generated by applying a deep learning network (e.g., the deep learning network 540 trained using the scheme 800) to map the per-channel ultrasound echo signals to beamformed data (e.g., the beamformed data 542 and 704). As can be observed, the ultrasound image 920 provides an improved contrast and resolution without a significant loss of cardiac structures (endocardium) compared to the ultrasound image 910. Accordingly, deep learning-based beamforming can provide a higher image quality or resolution than conventional DAS beamforming.

Figure 10:
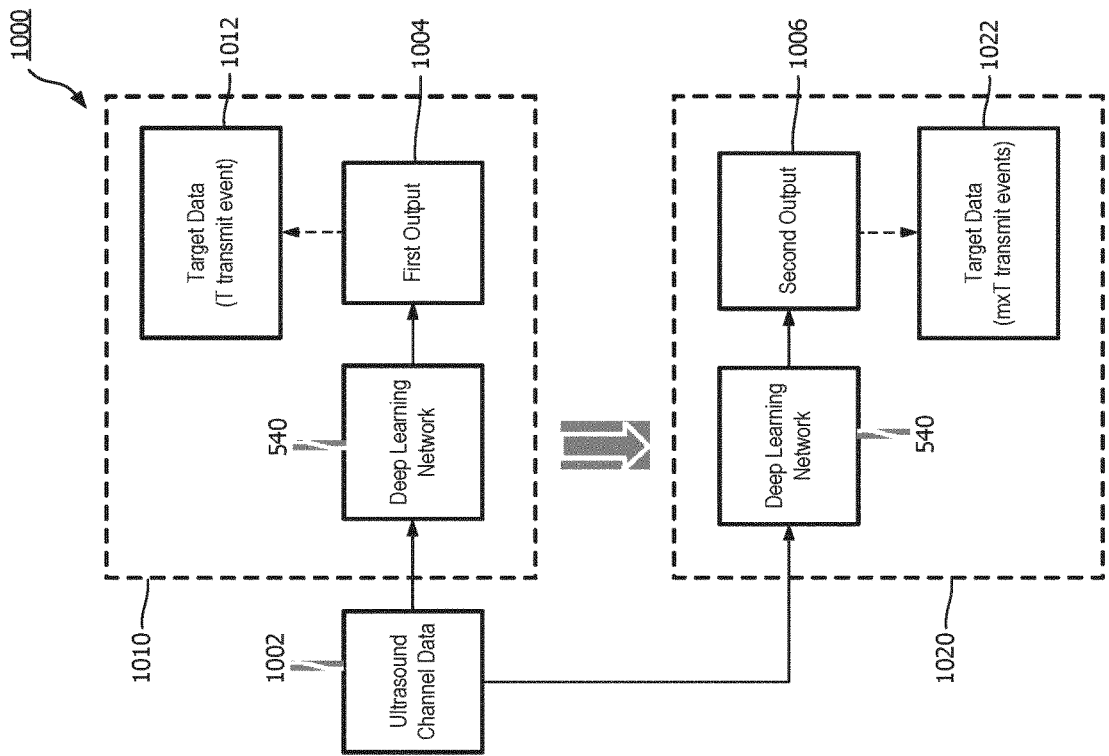
FIG. 10 is a schematic diagram illustrating a deep learning network training scheme, according to aspects of the present disclosure.

FIG. 10 is a schematic diagram illustrating a deep learning network training scheme 1000, according to aspects of the present disclosure. The scheme 1000 can be implemented by a computer system such as the host 130. The scheme 1000 can be employed to train the deep learning network 540 or the CNN 710 for ultrasound beamforming. The scheme 1000 is substantially similar to the scheme 800. However, the scheme 1000 uses different types of input and/or target data. The scheme 1000 trains the deep learning network 540 to predict or imitate beamformed data obtained from a greater number of transmit firings or events than the actual number of transmit firings used in an acquisition.

In the first stage 1010, the scheme 1000 trains the deep learning network 540 using an input-output pair, where the input includes ultrasound channel data 1002 and the output includes target beamformed data 1012. The ultrasound channel data 1002 may be normalized, time-aligned ultrasound echo channel signals similar to the normalized, time-aligned ultrasound echo channel signals 532. The ultrasound channel data 1002 may be acquired from T number of transmit events. For example, the transmission of an ultrasound beam is repeated T times and T sets of per-channel ultrasound echo signals are received. The ultrasound channel data 1002 may correspond to ultrasound echo responses received from a certain subject (e.g., the object 105).

In some examples, the ultrasound beams are focused beams (e.g., the focused ultrasound transmission beams 320). In some other examples, the ultrasound beams are unfocused beams or diverging beams (e.g., the unfocused ultrasound transmission beams 420).

In some examples, the ultrasound channel data 1002 can be a 3D dataset with an x-dimension corresponding to receive channels, a y-dimension corresponding to imaging depths, and a z-dimension corresponding to transmit events.

The target data 1012 may correspond to beamformed data generated from the ultrasound channel data 1002 using a DAS-based beamformer (e.g., the beamformer 114). The target data 1012 is also normalized so that the training does not have to learn amplitude mapping. During training, the deep learning network 540 can be applied to the ultrasound channel data 1002 using forward propagation to produce an output 1004 (e.g., the beamformed data 542). The coefficients of the filters 722 in the convolutional layers 720 and the weightings in the fully connected layers 730 can be adjusted using backward propagation to minimize the error between the output 1004 and the target output 1012. In some embodiments, the error function may be a MSE function or any other suitable error measure function. In other words, the scheme 1000 trains the deep learning network 540 to approximate the beamforming provided by the beamformer 114. The training or the adjusting of the coefficients for the filters 722 may be repeated for multiple input-output pairs. The first stage 1010 functions as an initialization of filter coefficients and/or weights in the deep learning network 540.

In the subsequent stage 1020, the scheme 1000 uses the filter coefficients and/or weights obtained for the deep learning network 540 from the first stage 1010 as a start and continues with the training. The scheme 1000 trains the deep learning network 540 using an input-output pair, where the input includes ultrasound channel data 1002 and the output includes target beamformed data 1022. The target data 1022 may correspond to beamformed data of the same subjected generated from ultrasound echo channel signals collected from a greater number of transmit events, for example, m×T number of transmit events or triggers, where m is greater than 1. Similarly, the target data 1022 is normalized data. In an example, the target data 1022 may be generated from 5 transmit events (e.g., with 5 repeated ultrasound transmissions) and the target data 1022 may be generated from 51 transmit events. Similar to the first stage 1020, the deep learning network 540 is trained by applying the ultrasound channel data 1002 using forward propagation to produce an output 1006 (e.g., the beamformed data 542). The coefficients of the filters 722 in the convolutional layers 720 and the weightings in the fully connected layers 730 can be adjusted using backward propagation to minimize the error between the output 1006 and the target output 1022. The training or the adjusting of the coefficients for the filters 722 may be repeated for multiple input-output pairs. While the scheme 1000 utilizes two stages of training, in some embodiments, the scheme 1000 may perform the second stage 1020 of training without performing the first stage 1010 of the training.

As can be observed, the scheme 1000 trains the deep learning network 540 to map per-channel ultrasound echo signals to beamformed data corresponding to a greater number of transmit events. Accordingly, the deep learning network 540 can provide a higher image quality than a conventional DAS-based beamformer (e.g., the beamformer 114). Further, when using diverging beams for unfocused imaging, the scheme 1000 can train the deep learning network 540 to compensate for artefacts caused by the use of diverging beams and improve the final ultrasound image quality without a significant increase in acquisition time.

Figure 11:
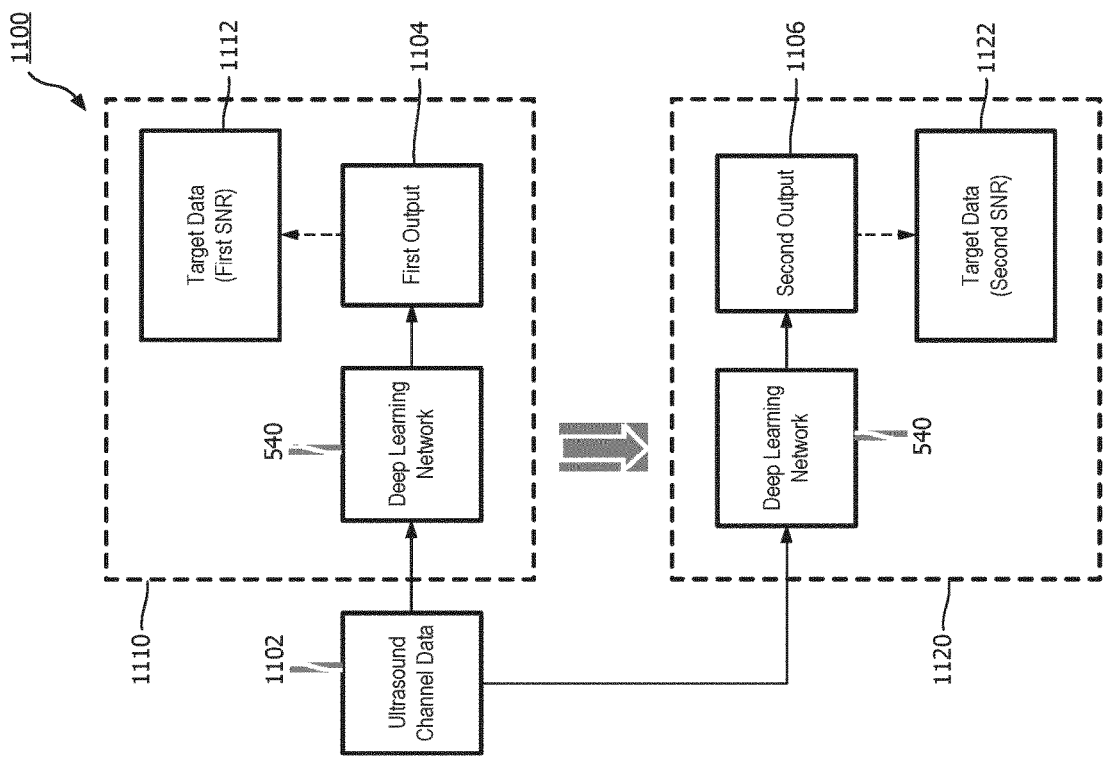
FIG. 11 is a schematic diagram illustrating a deep learning network training scheme, according to aspects of the present disclosure.

FIG. 11 is a schematic diagram illustrating a deep learning network training scheme 1100, according to aspects of the present disclosure. The scheme 1100 can be implemented by a computer system such as the host 130. The scheme 1100 can be employed to train the deep learning network 540 or the CNN 710 for ultrasound beamforming.

The scheme 1100 trains the deep learning network 540 in two stages 1110 and 1120. In the first stage 1110, the scheme 1100 trains the deep learning network 540 using an input-output pair, where the input includes ultrasound channel data 1102 and the output includes target beamformed data 1112. The ultrasound channel data 1102 may be normalized, time-aligned ultrasound echo channel signals similar to the normalized, time-aligned ultrasound echo channel signals 532. The ultrasound channel data 1102 may be acquired from a patient during a clinical setting or from a phantom in a test setup. The ultrasound channel data 1102 can be a 2D dataset with an x-dimension corresponding to receive channels and a y-dimension corresponding to imaging depths. The target data 1112 may correspond to beamformed data of the same subjected generated from the ultrasound channel data 1102 using a DAS-based beamformer (e.g., the beamformer 114). The target data 1112 may have a first SNR (e.g., S decibels (dB)). The target data 1112 is also normalized so that the training does not have to learn amplitude mapping. During training, the deep learning network 540 can be applied to the ultrasound channel data 1102 using forward propagation to produce an output 1104 (e.g., the beamformed data 542). The coefficients of the filters 722 in the convolutional layers 720 and the weightings in the fully connected layers 730 can be adjusted using backward propagation to minimize the error between the output 1104 and the target output 1112. In some embodiments, the error function may be a MSE function or any other suitable error measure function. In other words, the scheme 1100 trains the deep learning network 540 to approximate the beamforming provided by the beamformer 114. The training or the adjusting of the coefficients for the filters 722 may be repeated for multiple input-output pairs. The first stage 1110 functions as an initialization of filter coefficients and/or weights in the deep learning network 540

In the subsequent stage 1120, the scheme 1100 uses the filter coefficients and/or weights obtained for the deep learning network 540 from the first stage 1110 as a start and continues with the training. The scheme 1100 trains the deep learning network 540 using an input-output pair, where the input includes ultrasound channel data 1102 and the output includes target beamformed data 1122. The target data 1122 may correspond to beamformed data of the same subject, but with a second SNR higher than the first SNR (e.g., n×S dB, where n is greater than 1). The higher SNR can be due to the use of more advance signal and/or imaging processing techniques, a larger transducer aperture size, and/or a greater number of transmit firings. Similarly, the target data 1122 is normalized data. Similar to the first stage 1120, the deep learning network 540 is trained by applying the ultrasound channel data 1102 using forward propagation to produce an output 1106 (e.g., the beamformed data 542). The coefficients of the filters 722 in the convolutional layers 720 and the weightings in the fully connected layers 730 can be adjusted using backward propagation to minimize the error between the output 1106 and the target output 1122. The training or the adjusting of the coefficients for the filters 722 may be repeated for multiple input-output pairs. While the scheme 1100 utilizes two stages of training, in some embodiments, the scheme 1100 may perform the second stage 1120 of training without performing the first stage 1110 of the training.

As can be observed, the scheme 1100 trains the deep learning network 540 to map per-channel ultrasound echo signals to beamformed data corresponding to a higher SNR than beamformed data from a conventional DAS-based beamformer (e.g., the beamformer 114).

Figure 12:
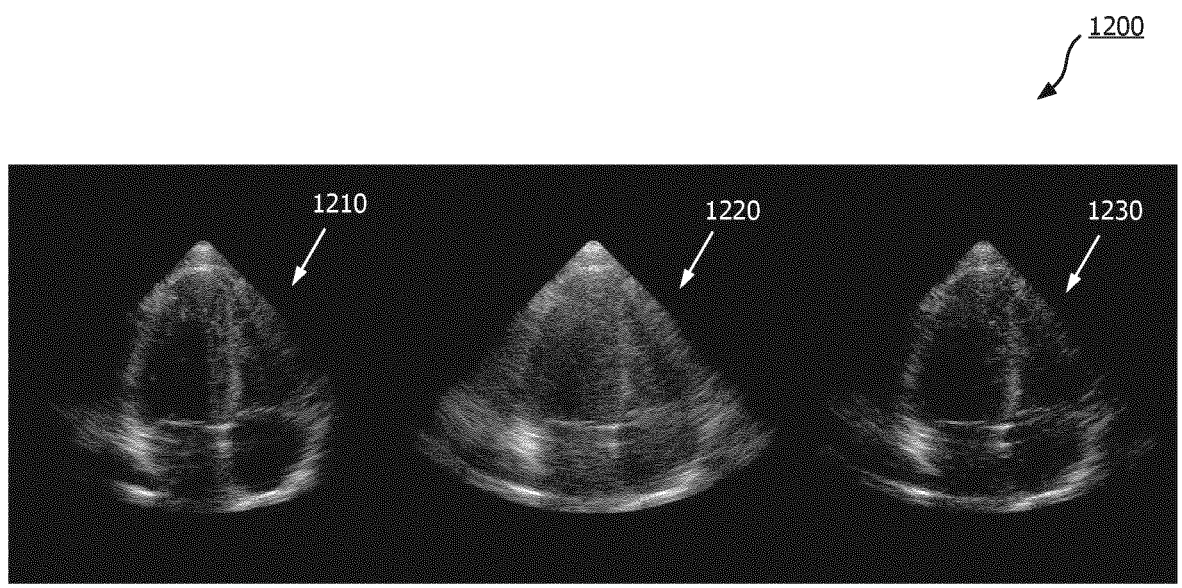
FIG. 12 illustrates images generated from DAS-based beamforming and deep learning-based beamforming, according to aspects of the present disclosure.

FIG. 12 illustrates ultrasound images generated from DAS-based beamforming and deep learning-based beamforming, according to aspects of the present disclosure. The ultrasound images 1210, 1220, and 1230 are acquired from in-vivo scan of a patient's heart. Initially, a first set of per-channel ultrasound echo signals (e.g., the digital ultrasound channel echo signals 162 and 502 and the ultrasound channel data 702 and 802) is collected after 5 transmit triggers of unfocused ultrasound beams or diverging beams (e.g., the unfocused ultrasound beam 420). Subsequently, a second set of per-channel ultrasound echo signals is collected after 51 transmit triggers of unfocused ultrasound beams or diverging beams. The ultrasound image 1210 is generated using a DAS-based beamformer (e.g., the beamformer 114) to beamform the second set of per-channel ultrasound echo signals from the 51 transmit triggers. The image 1220 is generated using the DAS beamformer to beamform the first set of per-channel ultrasound echo signals from the 5 transmit triggers. The image 1230 is generated by applying the deep learning network 540 to map the first set of per-channel ultrasound echo signals with the 5 transmit triggers to beamformed data (e.g., the beamformed data 542 and 704) from the 51 transmit triggers.

Comparing the image 1210 and the image 1220, the image 1210 from the 51 transmit triggers provides a higher image quality (e.g., better contrast, better contrast-to-noise) than the image 1220 from the 5 transmit triggers as expected. Comparing the image 1210, 1220, and 1230, the deep learning-based beamformed image 1230 from the 5 transmit triggers provides an image quality or resolution comparable to the DAS-based beamformed image 1210 from the 51 transmits triggers. The amount of clutters or artefacts in the image 1230 generated from the deep learning-based beamforming is significantly less than the image 1220 generated from the DAS-based beamforming with the same number of transmit triggers. Accordingly, deep learning-based beamforming can provide a higher image quality or resolution than conventional DAS-based beamforming.

In general, the schemes 800, 1000, and 1100 can use any suitable combination of simulation data generated offline, data acquired from a patient in a clinical setting, and data acquired from a phantom in a test setup to train the deep learning network 540. Given target beamformed data with a high SNR, for example, generated from a larger aperture size, an increased number of transmits, and/or coherently compounding echo signals received from the multiple transmits, the schemes 800, 1000, and 1100 can train the deep learning network 540 to output beamformed data with a higher SNR. In addition, using actual data acquired from an ultrasound system (e.g., the systems 100 and 200) instead of simulation data as input-output data pairs, the deep learning network 540 can be trained to suppress clutters from noise sources, such as acoustic noise, thermal noise, electronic noise, aberration, and/or reverberation, that are introduced due to poor acoustic conditions and cannot be addressed along the signal paths of the ultrasound system (e.g., the systems 100, 200, and/or 500).

In some embodiments, the deep learning network 540 can be trained to learn mapping of micro-beamformed data instead of per-channel ultrasound echo data to beamformed data. As an example, a system (e.g., the systems 100 and 200) may have 80 receive channels. The system may include micro-beamformers for micro-beamforming. For example, the system may group four adjacent acoustic elements (e.g., the acoustic elements 202) together and apply a beamformer to the group of acoustic elements to focus and steer delays to corresponding receive channels such that the micro-beamformed points are along the main axis of the transmit beam. Thus, after micro-beamforming, the 80 receive channels are reduced to 20 channels. The deep learning network 540 can be trained and applied to map the 20 micro-beamformed channel signals to beamformed data (e.g., the beamformed data 542) using substantially similar mechanisms as described above.

While the error functions or loss functions in the schemes 800, 1000, and 1100 described above are error or cost functions between the ground truth pixel values (e.g., in the target data 812, 822, 1012, 1022, 1112, and 1122) and the deep learning network 540 predicted pixel values (e.g., in the outputs 804, 806, 1004, 1006, 1104, and 1006), the deep learning network 540 can be trained to predict other signal values at an earlier stage (e.g., prior to beamforming) in the signal path of the ultrasound systems 100 and/or 200.

In an example, the deep learning network 540 can be trained to learn mapping transmit compounding from a limited number of transmits to an increased number of transmits. Thus, the loss function for the deep learning network 540 may be the difference between the ground truth transmit compounded channel data and network predicted compounded channel data corresponding to a greater number of transmits. For example, the input to the deep learning network 540 may be a 3D ultrasound echo channel dataset as described above, where with the x-dimension may correspond to receive channels, the y-dimension may correspond to imaging depths, and the z-dimension correspond to transmit events (e.g., T). The deep learning network 540 can be trained to output a compounded echo channel dataset corresponding to m×T transmits, where m greater than 1. Alternatively, the 3D ultrasound echo channel dataset can be converted to a 2D dataset by summing the per-channel ultrasound echo signals from the T transmit events (e.g., collapsed in the transmit or z-dimension) and the deep learning network 540 can be trained to provide the same compounded echo channel dataset corresponding to m×T transmits.

In general, the deep learning network 540 can output the compounded channel data or beamformed data in any suitable dimension or representations and the loss function can be modified accordingly. In an example of deep-learning based transmit compounding, the deep learning network 540 can be trained to provide a 1D compounded channel data collapsed in the transmit or z-dimension and sampled at the depth or y-dimension. In an example of deep-learning based beamforming, the deep learning network 540 can be trained to provide a 1D DAS vector collapsed in the channel or x-dimension and sampled in the depth or y-dimension or the scalar value of the corresponding pixel point collapsed in the channel or x-dimension and the transmit or z-dimension and sampled in the depth or y-dimension.

While the input data in the schemes 800, 1000, and 1100 described above is a 3D matrix for each pixel, a 3D matrix of aligned data for each beam may be used as input. The fully convolutional architecture may operate on the larger dataset using substantially similar mechanisms as described above.

While the input data in the schemes 800, 1000, and 1100 described above is per-channel ultrasound echo data, beamformed data can be used as input. For example, the input beamformed data may be produced from a limited number of transmits and may include grating lobe artefacts. The deep learning network 540 can be trained to provide beamformed data corresponding to a greater number of transmits and with a higher image quality and resolution.

Generally, aspects of the present disclosure describe using a machine learning network to replace one or more conventional ultrasound image processing steps, such as beamforming, that are required to generate conventional ultrasound images. The machine learning network is applied to the raw channel data obtained by the ultrasound transducer, rather than one or more of the conventional image processing steps being carried out on the raw channel data (e.g., beamforming and/or compounding of multiple transmits). The machine learning network is trained using a plurality of target beamformed data. Application of the machine learning network to the raw channel data results in modified data. A processor generates the ultrasound image using the modified data, which includes a trait of the target images (e.g., anatomical structure, speckle, etc.). While the disclosed embodiments are described in the context of mapping ultrasound echo channel data RF data to beamformed data using deep learning, in some embodiments, similar deep learning techniques can be applied to map ultrasound echo channel data in an intermediate frequency (IF) or baseband (BB) to beamformed data.

Figure 13:
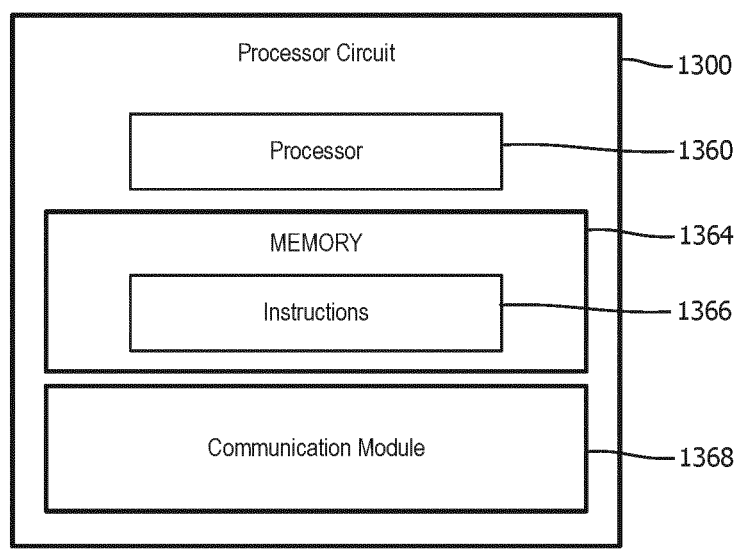
FIG. 13 is a schematic diagram of a processor circuit, according to embodiments of the present disclosure.

FIG. 13 is a schematic diagram of a processor circuit 1300, according to embodiments of the present disclosure. The processor circuit 1300 may be implemented in the probe 110 and/or the host 130 of FIG. 1. As shown, the processor circuit 1300 may include a processor 1360, a memory 1364, and a communication module 1368. These elements may be in direct or indirect communication with each other, for example via one or more buses.

The processor 1360 may include a CPU, a DSP, an ASIC, a controller, an FPGA, another hardware device, a firmware device, or any combination thereof configured to perform the operations described herein. The processor 1360 may also be implemented as a combination of computing devices, e.g., a combination of a DSP and a microprocessor, a plurality of microprocessors, one or more microprocessors in conjunction with a DSP core, or any other such configuration. In an example, the processor 1360 may correspond to the processor circuit 116 of FIG. 1. In an example, the processor 1360 may correspond to the processor circuit 134 of FIG. 1.

The memory 1364 may include a cache memory (e.g., a cache memory of the processor 1360), random access memory (RAM), magnetoresistive RAM (MRAM), read-only memory (ROM), programmable read-only memory (PROM), erasable programmable read only memory (EPROM), electrically erasable programmable read only memory (EEPROM), flash memory, solid state memory device, hard disk drives, other forms of volatile and non-volatile memory, or a combination of different types of memory. In an embodiment, the memory 1364 includes a non-transitory computer-readable medium. The memory 1364 may store instructions 1366. The instructions 1366 may include instructions that, when executed by the processor 1360, cause the processor 1360 to perform the operations described herein, for example, aspects of FIGS. 2-8, 10-11, and 14 and with reference to the host 130 and/or the probe 110 (FIG. 1). Instructions 1366 may also be referred to as code. The terms "instructions" and "code" should be interpreted broadly to include any type of computer-readable statement(s). For example, the terms "instructions" and "code" may refer to one or more programs, routines, sub-routines, functions, procedures, etc. "Instructions" and "code" may include a single computer-readable statement or many computer-readable statements. In an example, the memory 1364 may correspond to the memory 138 of FIG. 1.

The communication module 1368 can include any electronic circuitry and/or logic circuitry to facilitate direct or indirect communication of data between the processor circuit 1300, the probe 110, and/or the display 132. In that regard, the communication module 1368 can be an input/output (I/O) device. In some instances, the communication module 1368 facilitates direct or indirect communication between various elements of the processor circuit 1300 and/or the host 130 (FIG. 1). In some instances, the communication module 1368 may correspond to the communication interface 118 (FIG. 1). In some instances, the communication module 1368 may correspond to the communication interface 136 (FIG. 1).

Figure 14:
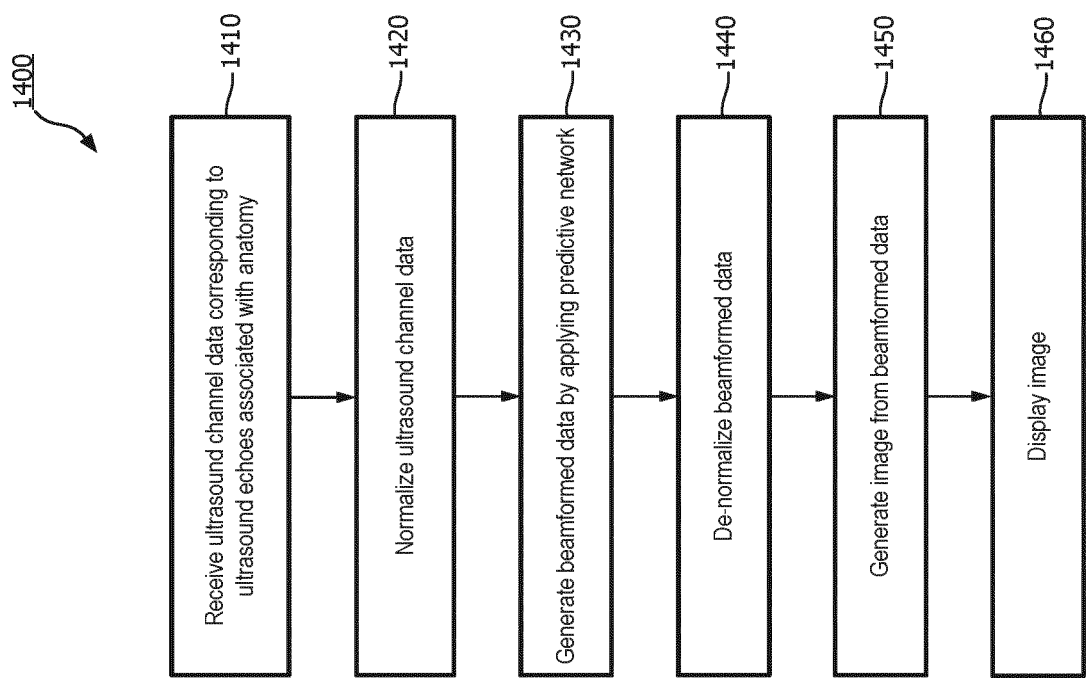
FIG. 14 is a flow diagram of a deep learning-based ultrasound imaging method, according to aspects of the present disclosure.

FIG. 14 is a flow diagram of a deep learning-base ultrasound imaging method 1400, according to aspects of the present disclosure. Steps of the method 1400 can be executed by the system 100, 200, and/or 500, for example, by a processor such as the processor circuits 116, 134, or the processor 1360, processor circuit such as the processor circuit 1300, and/or other suitable component such as the probe 110 and/or the host 130. As illustrated, the method 1400 includes a number of enumerated steps, but embodiments of the method 1400 may include additional steps before, after, and in between the enumerated steps. In some embodiments, one or more of the enumerated steps may be omitted or performed in a different order.

At step 1410, the method 1400 includes receiving, at a processor circuit in communication with an array of acoustic elements, ultrasound channel data corresponding to ultrasound echoes associated with an anatomy. The processor circuit may be similar to the processor circuits 116 and 138 and the processor circuit 1300. The acoustic elements may be similar to the acoustic elements 202. The ultrasound channel data may be similar to the digital ultrasound echo channel signals 162 and 502, the ultrasound channel data 702, 802, 1002, and 1102.

At step 1420, the method 1400 includes normalizing the ultrasound channel data by applying a first scaling function to the ultrasound channel data based on signal levels of the ultrasound channel data, for example, utilizing the normalization component 530 and/or the scheme 600.

At step 1430, the method 1400 includes generating beamformed data by applying a predictive network (e.g., the deep learning network 540) to the normalized ultrasound channel data (e.g., the ultrasound echo channel signals 532).

At step 1440, the method 1400 includes de-normalizing the beamformed data by applying a second scaling function to the beamformed data based on the signal levels of the ultrasound channel data, for example, utilizing the denormalization component 550.

In an example, the first scaling function may include scaling signal levels of the ultrasound channel data by a first factor corresponding a signal energy or an RIVIS value of the ultrasound channel data. The second scaling function may include scaling signal levels of the beamformed data by an inverse of the first factor (e.g., an inverse of the signal energy or the RMS value).

At step 1450, the method 1400 includes generating an image of the anatomy from the beamformed data.

At step 1460, the method 1400 includes outputting, to a display (e.g., the display 132) in communication with the processor circuit, the image of the anatomy.

In an embodiment, time delays are applied to the normalized ultrasound channel data based on an imaging depth, for example, utilizing the time-alignment component 520 to facilitate receive focusing.

In an embodiment, the ultrasound channel data includes a plurality of samples for a plurality of channels (e.g., the receive channels 1 to M of FIGS. 5 and 6). The beamformed data includes a plurality of output values (e.g., beamformed output sample or pixels 632). The normalization can include selecting a subset (e.g., the subset 610a, 610b, or 610c) of the plurality of samples based on an imaging depth and scaling a first signal level of a first sample (e.g., the sample 612a, 612b, or 612c) of the subset of the plurality of samples based on second signal levels (e.g., RMS) of the plurality of samples to produce a subset of the normalized ultrasound channel data (e.g., the subset 620a, 620b, or 620c). The first sample corresponds to a pixel location in the image. The generating the beamformed data includes applying the predictive network to the subset of the normalized ultrasound channel data to produce a first output value of the plurality of output values in the beamformed data, where the first output value correspond to the same pixel location in the image as the first sample.

In an embodiment, the array of acoustic elements includes a first aperture size (e.g., the aperture size 206) and the beamformed data is associated with a second aperture size larger than the first aperture size. For example, the prediction network is trained using the scheme 800.

In an embodiment, the ultrasound channel data is generated from a first quantity of ultrasound transmit trigger events and the beamformed data is associated with a second quantity of ultrasound transmit trigger events greater than the first quantity of ultrasound transmit trigger events. For example, the prediction network is trained using the scheme 1000.

In an embodiment, the ultrasound channel data is associated with a first SNR and the beamformed data is associated with a second SNR greater than the first SNR. For example, the prediction network is trained using the scheme 1100.

Aspects of the present disclosure can provide several benefits. For example, the use of a deep learning network (e.g., the deep learning network 540) for beamforming raw RF channel data (e.g., the ultrasound echo channel signals 162 and 502) acquired from a probe (e.g., the probes 110) can provide superior ultrasound image quality (e.g., improved resolution, enhanced contrast, and/or reduced side lobes, clutters and/or artefacts) compared to conventional DAS-based beamformers and/or reduce image acquisition time or improve imaging frame rates. The use of normalized, time-aligned ultrasound echo channel signals as inputs to the deep learning network allows the deep learning network to be trained for beamforming or beam-summing without having to learn amplitude mapping and/or time-delay mapping, and thus reduces the complexity of the network. Further, the use of the deep learning network can provide a computational cost advantage compared to conventional DAS-based beamformer (e.g., the beamformer 114) since operations in the inference stage of the deep learning network are mostly convolutions (e.g., multiply-adds) and matrix multiplications.

Persons skilled in the art will recognize that the apparatus, systems, and methods described above can be modified in various ways. Accordingly, persons of ordinary skill in the art will appreciate that the embodiments encompassed by the present disclosure are not limited to the particular exemplary embodiments described above. In that regard, although illustrative embodiments have been shown and described, a wide range of modification, change, and substitution is contemplated in the foregoing disclosure. It is understood that such variations may be made to the foregoing without departing from the scope of the present disclosure. Accordingly, it is appropriate that the appended claims be construed broadly and in a manner consistent with the present disclosure.

What is claimed is:
1. An ultrasound imaging system, comprising:
   an array of acoustic elements configured to transmit ultrasound energy into an anatomy and to receive ultrasound echoes associated with the anatomy; and
   a processor circuit in communication with the array of acoustic elements and configured to:

receive, from the array, ultrasound channel data corresponding to the received ultrasound echoes;
normalize the ultrasound channel data by applying a first scaling function to the ultrasound channel data based on signal levels of the ultrasound channel data;
generate beamformed data by applying a predictive network to the normalized ultrasound channel data;
de-normalize the beamformed data by applying a second scaling function to the beamformed data based on the signal levels of the ultrasound channel data;
generate an image of the anatomy from the beamformed data; and
output, to a display in communication with the processor circuit, the image of the anatomy.

2. The system of claim 1, wherein the processor circuit is further configured to:
apply time delays to the normalized ultrasound channel data based on an imaging depth.

3. The system of claim 1,
wherein the ultrasound channel data includes a plurality of samples for a plurality of channels,
wherein the beamformed data includes a plurality of output values,
wherein the processor circuit is further configured to select a subset of the plurality of samples based on an imaging depth,
wherein the processor circuit normalizing the ultrasound channel data includes scaling a first signal level of a first sample of the subset of the plurality of samples based on second signal levels of the subset of the plurality of samples to produce a subset of the normalized ultrasound channel data, and
wherein the processor circuit generating the beamformed data includes applying the predictive network to the subset of the normalized ultrasound channel data to produce a first output value of the plurality of output values in the beamformed data.

4. The system of claim 3, wherein the first sample and the first output value correspond to a same pixel location in the image.

5. The system of claim 4, wherein the processor circuit normalizing the ultrasound channel data includes:
scaling the first signal level of the first sample based on a root-mean-square (RMS) value of the subset of the plurality of samples.

6. The system of claim 1, wherein the array of acoustic elements includes a first aperture size, and wherein the beamformed data is associated with a second aperture size larger than the first aperture size.

7. The system of claim 6, wherein the predictive network is trained by:
providing test ultrasound channel data generated based on the first aperture size and first target beamformed data generated based on the second aperture size; and
training the predictive network to produce the first target beamformed data from the test ultrasound channel data.

8. The system of claim 7, wherein the predictive network is trained by:
providing second target beamformed data generated based on the first aperture size; and
training the predictive network to produce the second target beamformed data from the test ultrasound channel data before training the predictive network to produce the first target beamformed data.

9. The system of claim 1, wherein the ultrasound channel data is generated from a first quantity of ultrasound transmit trigger events, and wherein the beamformed data is associated with a second quantity of ultrasound transmit trigger events greater than the first quantity of ultrasound transmit trigger events.

10. The system of claim 9, wherein the predictive network is trained by:
providing test ultrasound channel data generated based on the first quantity of ultrasound transmit trigger events and first target beamformed data generated based on the second quantity of ultrasound transmit trigger events; and
training the predictive network to produce the first target beamformed data from the test ultrasound channel data.

11. The system of claim 10, wherein the predictive network is trained by:
providing second target beamformed data generated based on the first quantity of ultrasound transmit trigger events; and
training the predictive network to produce the second target beamformed data from the test ultrasound channel data before training the predictive network to produce the first target beamformed data.

12. The system of claim 1, wherein the ultrasound channel data is associated with a first signal-to-noise (SNR), and wherein the beamformed data is associated with a second SNR greater than the first SNR.

13. The system of claim 1, wherein the array of acoustic elements includes a one-dimensional array of acoustic elements.

14. The system of claim 1, wherein the array of acoustic elements includes a two-dimensional array of acoustic elements.

15. A method of ultrasound imaging, comprising:
receiving, at a processor circuit in communication with an array of acoustic elements, ultrasound channel data corresponding to ultrasound echoes associated with an anatomy;
normalizing the ultrasound channel data by applying a first scaling function to the ultrasound channel data based on signal levels of the ultrasound channel data;
generating beamformed data by applying a predictive network to the normalized ultrasound channel data;
de-normalizing the beamformed data by applying a second scaling function to the beamformed data based on the signal levels of the ultrasound channel data;
generating an image of the anatomy from the beamformed data; and
outputting, to a display in communication with the processor circuit, the image of the anatomy.

16. The method of claim 15, further comprising:
applying time delays to the normalized ultrasound channel data based on an imaging depth.

17. The method of claim 15,
wherein the ultrasound channel data includes a plurality of samples for a plurality of channels,
wherein the beamformed data includes a plurality of output values,
wherein the method includes selecting a subset of the plurality of samples based on an imaging depth,
wherein the normalizing the ultrasound channel data includes scaling a first signal level of a first sample of the subset of the plurality of samples based on second signal levels of the subset of the plurality of samples to produce the normalized ultrasound channel data, the first sample corresponding to a pixel location in the image, and
generating the beamformed data by applying the predictive network to the subset of the normalized ultrasound channel data to produce a first output value of the plurality of output values in the beamformed data, the first output value corresponding to the pixel location.

18. The method of claim 15, wherein the array of acoustic elements includes a first aperture size, and wherein the beamformed data is associated with a second aperture size larger than the first aperture size.

19. The method of claim 15, wherein the ultrasound channel data is generated from a first quantity of ultrasound transmit trigger events, and wherein the beamformed data is associated with a second quantity of ultrasound transmit trigger events greater than the first quantity of ultrasound transmit trigger events.

20. The method of claim 15, wherein the ultrasound channel data is associated with a first signal-to-noise (SNR), and wherein the beamformed data is associated with a second SNR greater than the first SNR.

* * * * *